(12) United States Patent
Ma et al.

(10) Patent No.: US 7,332,232 B2
(45) Date of Patent: Feb. 19, 2008

(54) OLEDS UTILIZING MULTIDENTATE LIGAND SYSTEMS

(75) Inventors: Bin Ma, Monroeville, PA (US); Robert Walters, Export, PA (US); Raymond Kwong, Plainsboro, NJ (US); Jason Brooks, Lambertville, NJ (US)

(73) Assignee: Universal Display Corporation, Ewing, NJ (US)

( * ) Notice: Subject to any disclaimer, the term of this patent is extended or adjusted under 35 U.S.C. 154(b) by 218 days.

(21) Appl. No.: 10/859,796

(22) Filed: Jun. 3, 2004

(65) Prior Publication Data

US 2005/0170207 A1 Aug. 4, 2005

Related U.S. Application Data

(63) Continuation-in-part of application No. 10/771,423, filed on Feb. 3, 2004, now abandoned.

(51) Int. Cl.
*H01L 51/54* (2006.01)
*C09K 11/06* (2006.01)

(52) U.S. Cl. ............. 428/690; 428/917; 313/504; 313/506; 257/E51.044; 546/4

(58) Field of Classification Search .......... None
See application file for complete search history.

(56) References Cited

U.S. PATENT DOCUMENTS

| | | | |
|---|---|---|---|
| 5,707,745 A * | 1/1998 | Forrest et al. ........... 428/432 |
| 6,303,238 B1 | 10/2001 | Thompson et al. ........ 428/690 |
| 6,653,654 B1 | 11/2003 | Che ........................ 257/40 |
| 2003/0059647 A1 * | 3/2003 | Thompson et al. ........ 428/690 |
| 2003/0068528 A1 * | 4/2003 | Thompson et al. ........ 428/690 |
| 2006/0134461 A1 * | 6/2006 | Huo et al. ................ 428/690 |
| 2006/0172146 A1 * | 8/2006 | Igarashi et al. ........... 428/690 |
| 2006/0182992 A1 * | 8/2006 | Nii et al. ................. 428/690 |

FOREIGN PATENT DOCUMENTS

WO WO 01/77667 A2 * 10/2001
WO WO 03/093283 A1 11/2003

OTHER PUBLICATIONS

Beeston et al. "Synthesis, Characterization, and Photochemical/Photophysical Properties of Ruthenium(II) Complexes with Hexadentate Bipyridine and Phenanthroline Ligands," Inorg. Chem., vol. 37, pp. 4368-4379 (1998).
Bardez et al. "Aluminum (III) Complexation by 8-Hydroxy-5-Sulfoquinoline and New Related Fluorogenic Ligands. A Time-Resolved Fluorescence Study," (2003).

* cited by examiner

*Primary Examiner*—Marie Yamnitzky
(74) *Attorney, Agent, or Firm*—Kenyon & Kenyon LLP

(57) ABSTRACT

An organic light emitting device is provided. The device has an anode, a cathode, and an organic layer disposed between the anode and the cathode. The organic layer comprises an emissive material having a transition metal and two or three bidentate ligands, which may be photoactive ligands. The bidentate photoactive ligands may be bound to the transition metal through a carbon-metal bond and a nitrogen-metal bond to form a cyclometallated ring. The organic layer may have the formula $LX_a\text{-}(L)_bM$, wherein X is a linking group that links two or more ligand L and M is a metal.

47 Claims, 15 Drawing Sheets

OLEDS UTILIZING MULTIDENTATE LIGAND SYSTEMS

REFERENCE TO RELATED APPLICATIONS

This application is a continuation-in-part of U.S. application Ser. No. 10/771,423 filed Feb. 3, 2004 now abandoned.

JOINT RESEARCH AGREEMENT

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to efficient organic light emitting devices (OLEDs), and more specifically to phosphorescent organic materials used in such devices. More specifically, the present invention relates to phosphorescent emitting materials with improved stability and efficiency when incorporated into an OLED

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials-that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

Industry standards call for the lifetime of full color displays to be at least about 5000 hours. In addition, high stability and efficiency are important characteristics of high quality displays. These requirements have helped generate a need for materials that exhibit longer lifetimes, higher stability, and higher efficiency than have been generally achieved in the prior art.

SUMMARY OF THE INVENTION

The present invention provides an organic light emitting device that has an anode, a cathode and one or more organic layers between the anode and the cathode. The present invention also provides materials having improved stability for use in an OLED. The materials are metal complexes comprising a multidentate ligand system.

In one embodiment, the organic layer comprises an emissive layer comprising an emissive material which is a phosphorescent organometallic emissive material. The phosphorescent emissive material comprises a metal bound to two or more ligands wherein at least one ligand is a photoactive ligand and a wherein two or more of the ligands are covalently linked by one or more linking groups. Preferably, the phosphorescent emissive material comprises a transition metal bound to two or three bidentate ligands, wherein two or more of the bidentate ligands are covalently linked by one or more linking groups. Preferred emissive materials of the present invention may be represented by the formula I

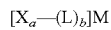 (I)

wherein M is a metal, L is a bidentate ligand, X is a linking group that links two or more L, a is 1 to 4, and b is 2 or 3. The bidentate ligands are selected from bidentate photoactive ligands, and bidentate ancillary ligands. The emissive materials comprise at least one bidentate photoactive ligand.

In one embodiment, the device has an emissive layer comprising an emissive material which is a phosphorescent organometallic emissive material. The phosphorescent organometallic emissive material comprises a transition metal, and two or three bidentate ligands, wherein two or more of the bidentate ligands are covalently linked by a linking group. The bidentate ligands are selected from (i) bidentate photoactive ligands, wherein each bidentate photoactive ligand is bound to the transition metal through a carbon-metal bond and a nitrogen-metal bond to form a cyclometallated ring, and (ii) bidentate ancillary ligands, wherein at least one of the ligands is a bidentate photoactive ligand.

In one embodiment, the invention provides an organic light emitting device comprising an anode, a cathode, and an organic layer disposed between the anode and the cathode, wherein the organic layer comprises a metal complex having a first ligand, which is a bidentate ligand, a second ligand, and a linking group that covalently links the first ligand and the second ligand. The linking group does not provide π-conjugation between the first ligand and the second ligand. The non-conjugated linking group may comprise at least one atom in the linkage which contains no π-electrons, such as an $sp^3$ hybridized carbon or silicon. The second ligand may be a bidentate ligand or may be a monodentate ligand. The metal complex may further comprises an additional monodentate or bidentate ligand. The additional ligand may also be linked to the first ligand, to second ligand, or to both the first ligand and the second ligand.

In another embodiment, the invention provides an organic light emitting device comprising an anode, a cathode, and an organic layer disposed between the anode and the cathode, wherein the organic layer comprises an emissive material having the formula I

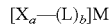 (I)

wherein,

M is a transition metal having a molecular weight greater than 40;

X is a linking group that links two or more L, and is selected from the group consisting of —(CR$_2$)$_d$—, —[O(CR$_2$)$_e$]O—, or a group having the formula

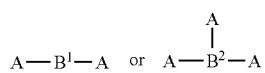

wherein

A is —(CR$_2$)$_f$—, or -Z-(CR$_2$)$_g$—;

Z is —O—, —NR—, or —SiR$_2$—;

B$^1$ is —O—, —NR—, —CR=CR—, aryl, heteroaryl, cycloalkyl, or a heterocyclic group, B$^2$ is

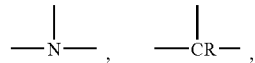

alkyl, aryl, heteroaryl, cycloalkyl, or a heterocyclic group;

each R is independently selected from H, alkyl, aralkyl, aryl and heteroaryl, d is 1 to 6, e is 1 to 6, f is 1 to 4, and g is 1 to 4;

L is a bidentate ligand selected from the group consisting of (i) bidentate photoactive ligands having the formula II

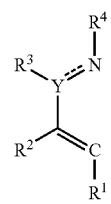 (II)

wherein

Y is N or C, the dotted line represents an optional double bond,

R$^1$, R$^2$, R$^3$ and R$^4$ are independently selected from H, alkyl, or aryl, and additionally or alternatively, one or more of R$^1$ and R$^2$, R$^2$ and R$^3$, and R$^3$ and R$^4$ together from independently a 5 or 6-member cyclic group, wherein said cyclic group is cycloalkyl, cycloheteroalkyl, aryl or heteroaryl; and wherein said cyclic group is optionally substituted by one or more substituents Z;

each substituent Z is independently selected from the group consisting of alkyl, alkenyl, alkynyl, aralkyl, CN, CF$_3$, NR$_2$, NO$_2$, OR, halo, and aryl, and additionally, or alternatively, two Z groups on adjacent ring atoms form a fused 5- or 6-membered aromatic group, and each R is independently selected from H, alkyl, aralkyl, aryl and heteroaryl.

(ii) bidentate ancillary ligands, a is 1 to 4;

b is 2 or 3; and at least one L is selected from a bidentate photoactive ligand.

In another embodiment, the invention provides an organic light emitting device comprising an anode, a cathode, and an organic layer disposed between the anode and the cathode, wherein the organic layer comprises a material of the formula VII

 (VII)

wherein

Q is a bidentate ligand of the formula VIII

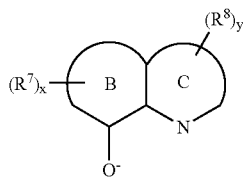

wherein
- ring B is a 5- or 6-membered aromatic group,
- ring C is a 5- or 6-membered aromatic heterocyclic ring with at least one nitrogen atom that coordinates to the Al,
- each $R^7$ is independently selected from the group consisting of alkyl, alkenyl, alkynyl, aralkyl, CN, $CF_3$, $NR_2$, $NO_2$, OR, halo, and aryl, and additionally, or alternatively, two $R^7$ groups on adjacent ring atoms form a fused 5- or 6-membered aromatic group,
- each $R^8$ is independently selected from the group consisting of alkyl, alkenyl, alkynyl, aralkyl, CN, $CF_3$, $NR_2$, $NO_2$, OR, halo, and aryl, and additionally, or alternatively, two $R^8$ groups on adjacent ring atoms form a fused 5- or 6-membered aromatic group,
- each R is independently selected from H, alkyl, aralkyl, aryl and heteroaryl,
- x is 0 to 3, and
- y is 0 to 3;
- J is selected from monodentate ligands having the formula

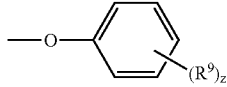

wherein each $R^9$ is independently selected from the group consisting of alkyl, alkenyl, alkynyl, aralkyl, CN, $CF_3$, $NO_2$, O-alkyl, halo, and aryl, and z is 0 to 5;
- X is a linking group as defined for Formula I that links two or more of the ligands Q or J wherein at least one of the ligands linked by the linking group X is a bidentate ligand Q;
- h is 2 or 3;
- i is 1 to 4; and
- j is 0 to 2.

DETAILED DESCRIPTION

Figure 1:
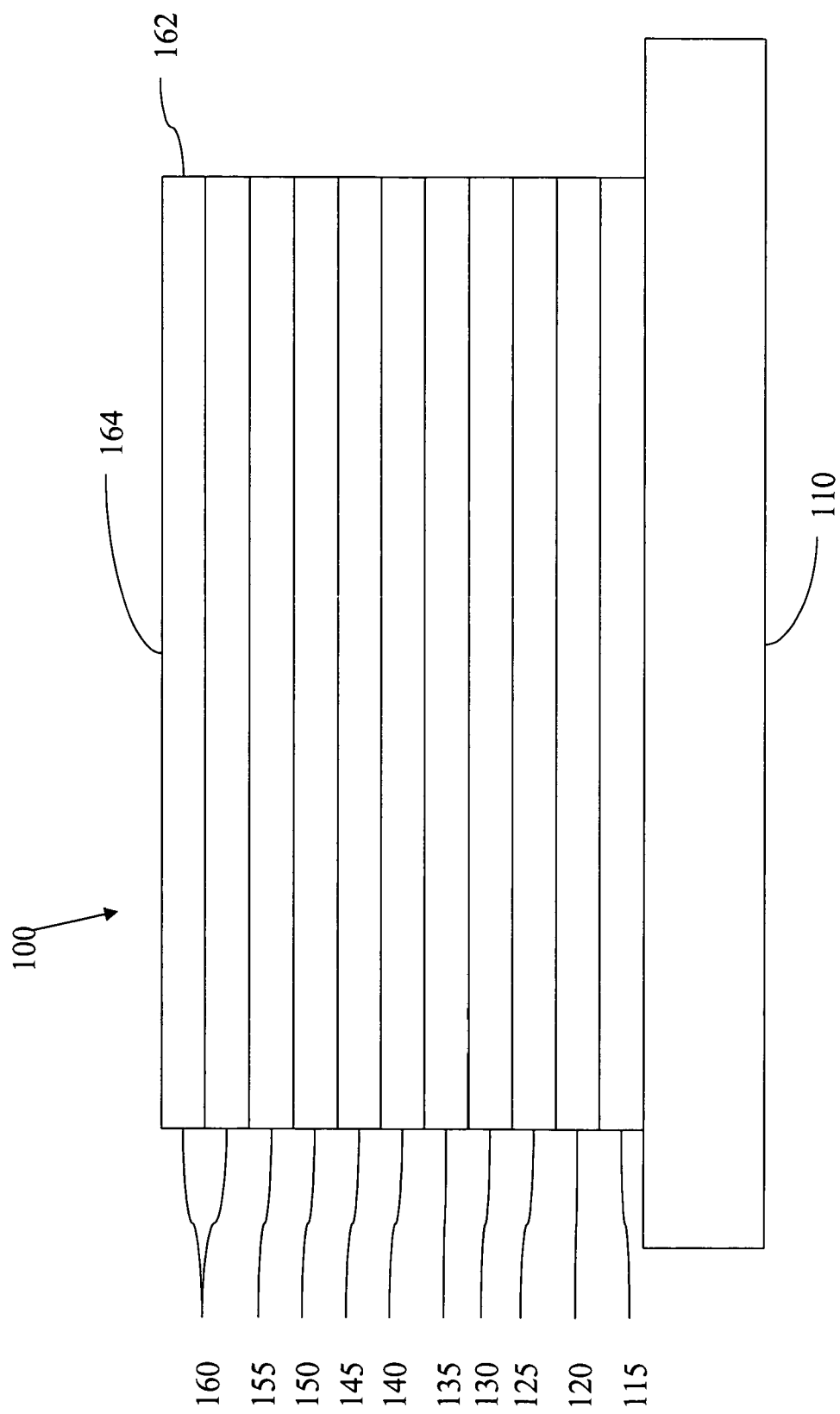
FIG. 1 shows an organic light emitting device having separate electron transport, hole transport, and emissive layers, as well as other layers.

The present invention provides an organic light emitting device that has an anode, a cathode and one or more organic layers between the anode and the cathode. The present invention also provides materials having improved stability for use in an OLED. The materials are metal complexes comprising a multidentate ligand system. By linking individual ligands together to form a multidentate ligand system, it is possible to increase the stability of the metal complexes formed using the ligands. In one embodiment, the device has an emissive layer comprising an emissive material which is a phosphorescent organometallic emissive material. Previously used phosphorescent emissive materials, such as Ir(ppy)$_3$, use individual bidentate ligands. The phosphorescent emissive material in the present invention is composed of a heavy metal atom and a multidentate ligand system such as a tetradentate or hexadentate ligand system formed, for example, by linking bidentate ligands.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak The term "organometallic" as used herein is as generally understood by one of ordinary skill in the art and as given, for example, in "Inorganic Chemistry" (2nd Edition) by Gary L. Miessler and Donald A. Tarr, Pentice-Hall (1998). Thus, the term organometallic refers to compounds which have an organic group bonded to a metal through a carbon-metal bond. This class does not include per se coordination compounds, which are substances having only donor bonds from heteroatoms, such as metal complexes of anines, halides, pseudohalides (CN, etc.), and the like. In practice organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 125 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003/0230980, which is incorporated by reference in its entirety. Other hole transport layers may be used.

Emissive layer 135 comprises an organic dopant material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material. The host material may be capable of transporting electrons and/or holes, and is doped with the emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. Other emissive layer materials and structures may be used.

Electron transport layer 140 may include a material capable of transporting electrons. Electron transport layer 140 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in U.S. patent application Publication No. 2003/0230980, which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) level of the electron transport layer. The "charge carrying component" is the material responsible for the LUMO that actually transports electrons. This component may be the base material, or it may be a dopant. The LUMO level of an organic material may be generally characterized by the electron affinity of that material and the relative electron injection efficiently of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2, and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive region. An electron blocking layer 130 may be disposed between emissive region 135 and the hole transport layer 125, to inhibit electrons from leaving emissive region 135 in the direction of hole transport layer 125. Similarly, a hole blocking layer 140 may be disposed between emissive region 135 and electron transport layer 145, to inhibit holes from leaving emissive region 135 in the direction of electron transport layer 140. Blocking layers may also be used to inhibit excitons from diffusing out of the emissive region. The theory and use of blocking layers is described in more detail in U.S. Pat. No. 6,097,147 and U.S. patent application Publication No. 2003/0230980, which are incorporated by reference in their entireties.

As used herein, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. Pat. No. 7,071,615, which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. Pat. No. 7,071,615, which is incorporated by reference in its entirety.

Figure 2:
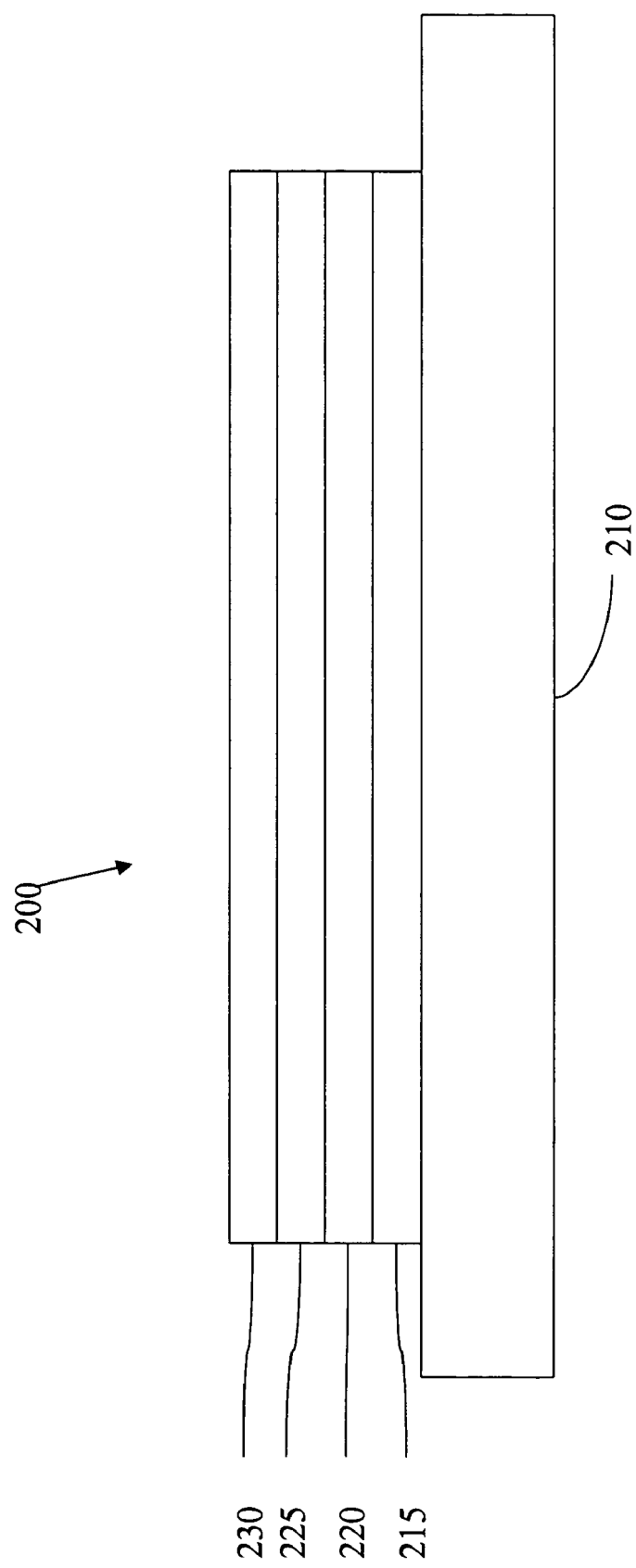
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Patent No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In one embodiment of the invention, the emissive materials are phosphorescent organometallic emissive materials. The phosphorescent emissive material is composed of a heavy metal atom and a multidentate, for example a tetradentate or hexadentate ligand system. By linking two or three bidentate ligands together to give tetradentate or hexadentate ligand systems, it is possible to increase the stability of the metal complexes formed using the ligands.

The phosphorescent emissive material comprises a transition metal bound to two or three bidentate ligands, wherein two or more of the bidentate ligands are covalently linked by one or more linking groups. The emissive materials of the present invention may be represented by the formula I $$[X_a\text{---}(L)_b]M \tag{I}$$

wherein M is a metal, L is a bidentate ligand, X is a linking group that links two or more L, a is 1 to 4, and b is 2 or 3. The bidentate ligands are selected from bidentate photoactive ligands, and bidentate ancillary ligands. The emissive materials comprise at least one bidentate photoactive ligand.

The metal, M, is selected from the transition metals having an atomic weight greater than 40, Tl, P, Bi, In, Sn, Sb and Te. Preferred transition metals include Ir, Pt, Pd, Rh, Re, Os, Au, and Ag. More preferably, the metal is Ir or Pt. Most preferably, the metal is Ir.

The emissive materials of the present invention may comprise carbene-metal complexes including those disclosed in United States Patent Publication No. 2005-0260441, which is incorporated in its entirety by reference, wherein a carbene ligand is preferably linked to another ligand by a linking group.

The emissive materials of the present invention comprise at least one photoactive ligand. This ligand is referred to as "photoactive" because it is believed that it contributes to the photoactive properties of the emissive material.

In one embodiment of the invention, a photoactive ligand may be represented by the formula II

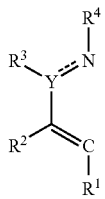

(II)

wherein
Y is N or C,
the dotted line represents an optional double bond,
$R^1$, $R^2$, $R^3$ and $R^4$ are independently selected from H, alkyl, or aryl, and additionally or alternatively, one or more of $R^1$ and $R^2$, $R^2$ and $R^3$, and $R^3$ and $R^4$ together from independently a 5 or 6-member cyclic group, wherein said cyclic group is cycloalkyl, cycloheteroalkyl, aryl or heteroaryl; and wherein said cyclic group is optionally substituted by one or more substituents Z; each substituent Z is independently selected from the group consisting of alkyl, alkenyl, alkynyl, aralkyl, CN, $CF_3$, $NR_2$, $NO_2$, OR, halo, and aryl, and additionally, or alternatively, two Z groups on adjacent ring atoms form a fused 5- or 6-membered aromatic group, and each R is independently selected from H, alkyl, aralkyl, aryl and heteroaryl.

The photoactive ligand of the formula II is a bidentate ligand that is bound to the transition metal through a carbon-metal bond and a nitrogen-metal bond to form a cyclometallated ring as shown in the partial structure III

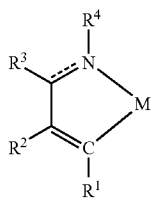

(III)

wherein Y, M, $R^1$, $R^2$, $R^3$ and $R^4$ are as described above for formula II.

In a preferred embodiment, at least one of $R^2$ and $R^2$ or $R^3$ and $R^4$ together form a 5 or 6-membered aryl ring. In a more preferred embodiment, both $R^1$ and $R^2$ together form a 5 or 6-membered aryl ring, and $R^3$ and $R^4$ together from a 5 or 6-member aryl ring.

In a further embodiment, $R^1$ and $R^2$ together form a phenyl ring, and $R^3$ and $R^4$ together form a heteroaryl group to give a bidentate photoactive ligand of the formula IV

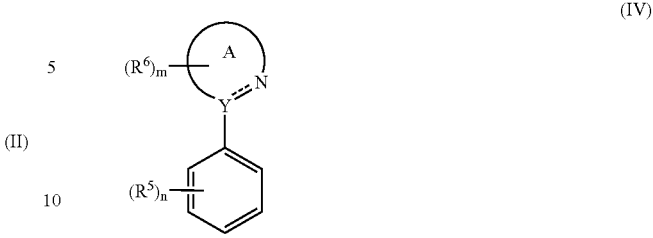

(IV)

wherein:
ring A is an aromatic heterocyclic ring or a fused aromatic heterocyclic ring with at least one nitrogen atom that coordinates to the metal M,
Y is selected from carbon or nitrogen,
each $R^5$ is independently selected from the group consisting of alkyl, alkenyl, alkynyl, aralkyl, CN, $CF_3$, $NR_2$, $NO_2$, OR, halo, and aryl, and additionally, or alternatively, two $R^5$ groups on adjacent ring atoms form a fused 5- or 6-membered aromatic group,
each $R^6$ is independently selected from the group consisting of alkyl, alkenyl, alkynyl, aralkyl, CN, $CF_3$, $NR_2$, $NO_2$, OR, halo, and aryl, and additionally, or alternatively, two $R^6$ groups on adjacent ring atoms form a fused 5- or 6-membered aromatic group,
each R is independently selected from H, alkyl, aralkyl, aryl and heteroaryl,
n is 0 to 4, and
m is 0 to 4.

Ring A in formula IV is an aromatic heterocyclic ring or a fused aromatic heterocyclic ring with at least one nitrogen atom that is coordinated to the metal M, wherein the ring can be optionally substituted. In a preferred embodiment, A is pyridine, pyrimidine, quinoline, or isoquinoline. Most preferable, A is pyridine. Optional substituents on the Ring A include of alkyl, alkenyl, alkynyl, aralkyl, CN, $CF_3$, $NR_2$, $NO_2$, OR, halo, and aryl. A particularly preferred photoactive ligand is phenylpyridine, and derivatives thereof.

The number of photoactive ligands may be any integer from 1 to the maximum number of ligands that may be attached to the metal. For example, for Ir the maximum number of bidentate ligands bound to the metal would 3, at least one of which would be a photoactive ligand. When more that one photoactive ligand is present, each photoactive ligand may be the same or may be different.

The emissive materials of the present invention may comprise one or more ancillary ligands. These ligands are referred to as "ancillary" because it is believed that they may modify the photoactive properties of the molecule, as opposed to directly contributing to the photoactive properties. The definitions of photoactive and ancillary are intended as non-limiting theories. Ancillary ligands for use in the emissive material may be selected from those known in the art. Non-limiting examples of ancillary ligands may be found in PCT Application Publication WO 02/15645 A1 to Lamansky et al. at pages 89-90, which is incorporated herein by reference. Preferred ancillary ligands include acetylacetonate (acac) and picolinate (pic), and derivatives thereof. The preferred ancillary ligands have the following structures:

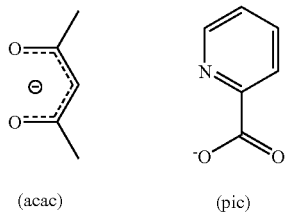

(acac)    (pic)

The number of "ancillary" ligands of a particular type, may be any integer from zero to one less than the maximum number if ligands that may be attached to the metal.

In one embodiment, the linking group, X, links two bidentate ligands to give a tetradentate ligand system. The tetradentate ligand system may be represented by the formula (V)

L-X-L                                                                                     (V)

wherein each L is independently selected from a bidentate photoactive ligand and a bidentate ancillary ligand, and X is a linking group. The tetradentate ligand system may be comprised of two photoactive ligands, two ancillary ligands, or a photoactive ligand and an ancillary ligand. The tetradentate ligand system binds to the metal through four chemical bonds in the emissive material. The emissive material may further comprise an additional bidentate ligand that is not linked to the tetradentate ligand system, and which may be a bidentate ancillary ligand, or a bidentate photoactive ligand. In the case where the tetradentate ligand system is comprised of two ancillary ligands, the emissive material comprising the tetradentate ligand system further comprises a separate photoactive ligand bound to the metal. The linking group, X, may be connected to each bidentate ligand, L, by a covalent bond to any carbon or heteroatom of the ligand that does not interfere with the ligands ability to bind to the metal, M, and form a tetradentate system. For example, the case where the tetradentate ligand system is comprised of two phenylpyridine ligands linked by a linking group, X, is depicted below:

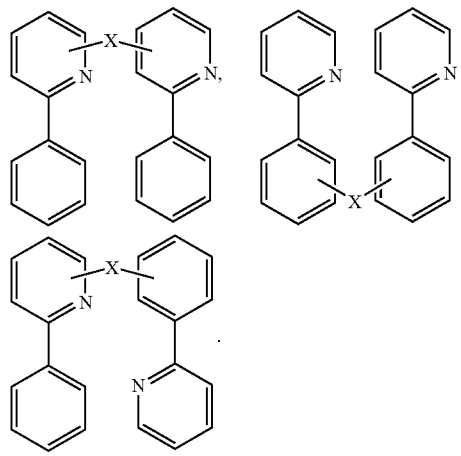

The linking group may be covalently bound to any atom of the phenylpyridine that does not interfere with each ligand's ability to bind to the metal in a bidentate fashion to form a tetra dentate ligand system. Thus, for example, the linking group may not be bound to the pyridine nitrogen.

In another embodiment of the invention, the emissive material comprises a hexadentate ligand system. The linking group may link two tridentate ligands or three bidentate ligands or a bidentate and a tetradentate ligand to form a hexadentate ligand system. In one embodiment, the hexadentate ligand system comprises one or more linking groups, X, that link three bidentate ligands. Such hexadentate ligand systems may be represented by the formula VI$_a$ and VI$_b$ L—X—L—X—L                                                                    (VI$_a$)

L—X—L                                                                                (VI$_b$)
     |
     L wherein each X is independently selected from a linking group, and each L is independently selected from a bidentate photoactive ligand and a bidentate ancillary ligand, with the proviso that at least one L is selected from a bidentate photoactive ligand. The hexadentate ligand system may be comprised of three photoactive ligands, two photoactive ligands and an ancillary ligand, or one photoactive ligand and two ancillary ligands. The hexadentate ligand system binds to the metal through six chemical bonds in the emissive material. The linking group(s), X, may be connected to each bidentate ligand, L, by a covalent bond to any carbon or heteroatom of the ligand that does not interfere with the ligand's ability to bind to the metal, M, and form a hexadentate system. Examples of the case where the hexadentate ligand system is comprised of three phenylpyridine ligands linked by a linking group(s), X, are depicted below:

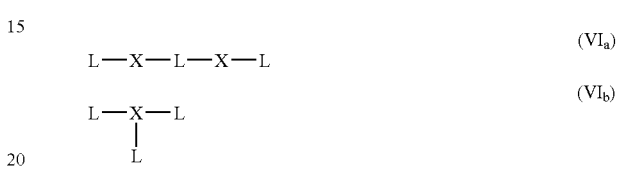

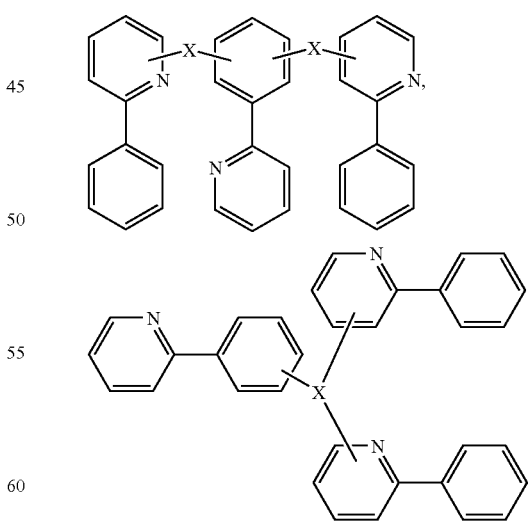

In another embodiment, the emissive material comprises a hexadentate ligand system having three phenylpyridine ligands linked by a linking group(s), X, through the phenyl rings as depicted below:

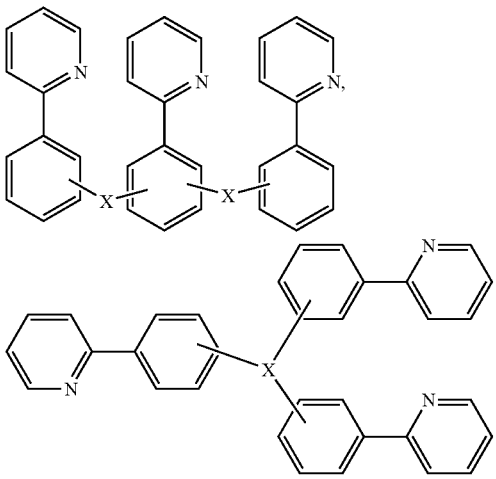

In another embodiment, the emissive material comprises a hexadentate ligand system having three phenylpyridine ligands linked by a linking group(s), X, through the pyridine rings as depicted below:

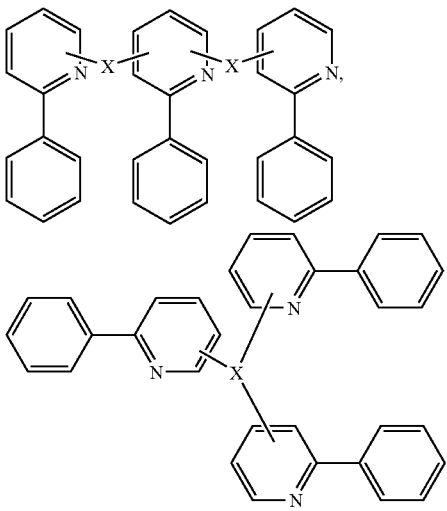

In other embodiments of the invention, other structures with multidentate ligands can be useful in OLED applications. For example, electron transporters using derivatives of aluminum 8-hydroxyquinolates, such as Alq and BAlq, can be ligand-interlinked, preferably by non-conjugated linking groups. Such materials may be used in an OLED as an electron transporting material and/or as a host material in an emissive layer. Linking according to the present invention may improve the stability of devices containing these compounds as compared to devices containing the non-ligand-interlinked analogs. These materials may be represented by the formula VII

 (VII)

wherein Q is a bidentate ligand, J is a monodentate ligand, X is a linking group, h is 2 or 3, i is 1 to 4 and j is 0 to 2. The linking group X links two or more of the ligands, Q or J, wherein at least one of the ligands linked by the linking group X is a bidentate ligand Q.

The compound of formula VII comprise two or three bidentate ligands, Q, that may be represented by the formula VIII

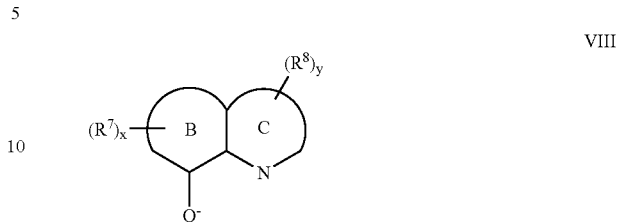

wherein
ring B is a 5- or 6-membered aromatic group,
ring C is a 5- or 6-membered aromatic heterocyclic ring with at least one nitrogen atom that coordinates to the metal M,
each $R^7$ is independently selected from the group consisting of alkyl, alkenyl, alkynyl, aralkyl, CN, $CF_3$, $NR_2$, $NO_2$, OR, halo, and aryl, and additionally, or alternatively, two $R^7$ groups on adjacent ring atoms form a fused 5- or 6-membered aromatic group,
each $R^8$ is independently selected from the group consisting of alkyl, alkenyl, alknyl, aralkyl, CN, $CF_3$, $NR_2$, $NO_2$, OR, halo, and aryl, and additionally, or alternatively, two $R^8$ groups on adjacent ring atoms form a fused 5- or 6-membered aromatic group,
each R is independently selected from H, alkyl, aralkyl, aryl and heteroaryl,
x is 0 to 3, and
y is 0 to 3.

The bidentate ligand Q is bound to the aluminum through an oxygen-metal bond and a nitrogen-metal bond to form the partial structure IX

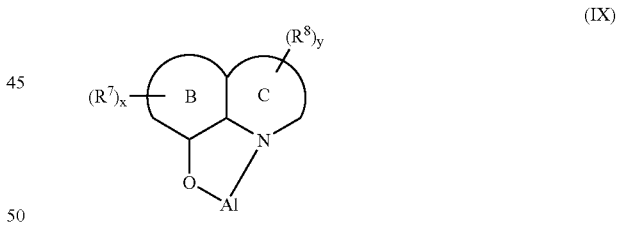

wherein $R^7$, $R^8$, x and y are as described above for formula VIII.

In a preferred embodiment, ring B is a phenyl ring and ring C is a pyridine ring providing a bidentate ligand of formula X

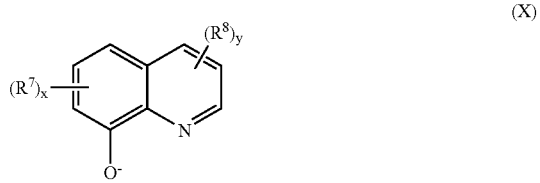

The ligand J is selected from monodentate ligands having the formula

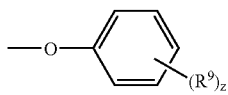

wherein each $R^9$ is independently selected from the group consisting of alkyl, alkenyl, alkynyl, aralkyl, CN, $CF_3$, $NO_2$, O-alkyl, halo, and aryl, and z is 0 to 5.

In one embodiment, the linking group, X, links two bidentate ligands Q to give a tetradentate ligand system. The tetradentate ligand system may be represented by the formula (XI)

Each bidentate ligand Q may be the same or may be different. The complex may further comprise an additional bidentate ligand Q that is not linked to the tetradentate ligand system. Alternatively the complex may further comprise a monodentate ligand J that is not linked to the tetradentate ligand system. The linking group, X, may be connected to each bidentate ligand, Q, by a covalent bond to any carbon or heteroatom of the ligand that does not interfere with the ligand's ability to bind to the Al, and form a tetradentate system. For example, the case where the tetradentate ligand system is comprised of two 8-hydroxyquinolinato ligands linked by a linking group, X, is depicted below:

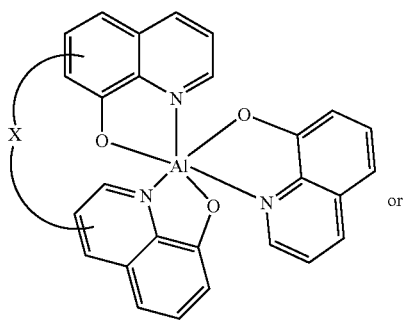

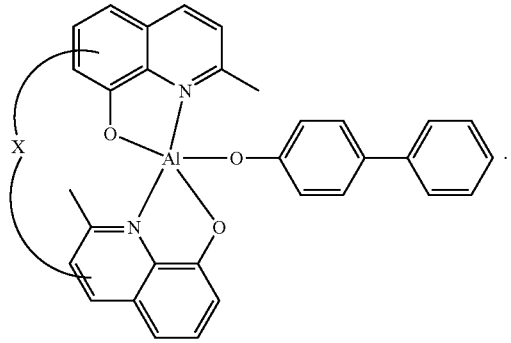

In another embodiment, the linking group, X, links a bidentate ligands Q to a monodentate ligand J to give a tridentate ligand system. The tridentate ligand system may be represented by the formula (XII)

The complex may further comprise an additional bidentate ligand Q that is not linked to the tridentate ligand system. The linking group, X, may be connected to each ligand in the tridentate ligand system by a covalent bond to any carbon or heteroatom of the ligand that does not interfere with the ligand's ability to bind to the Al, and form a tridentate system. For example, the case where the tridentate ligand system is comprised of a 8-hydroxyquinolinato ligand linked by a linking group, X, to a 4-phenylphenolate ligand is depicted below:

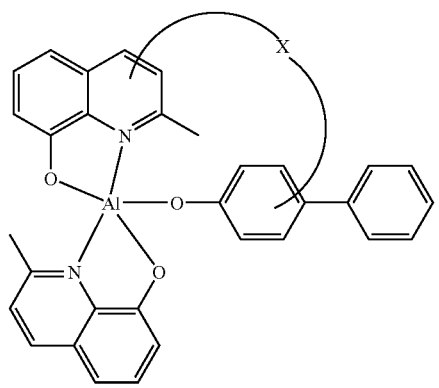

In another embodiment of the invention, one or more linking groups, X, link three bidentate ligands Q to give a hexadentate ligand system that may be represented by the formula $XIII_a$ and $XIII_b$

wherein each X is independently selected form a linking group, and each bidentate ligand Q may be the same or may be different. The linking group(s), X, may be connected to each bidentate ligand, Q, by a covalent bond to any carbon or heteroatom of the ligand that does not interfere with the ligand's ability to bind to the Al and form a hexadentate system. Examples of the case where the hexadentate ligand system is comprised of three 8-hydroxyquinolinato ligands linked by a linking group(s), X, are depicted below:

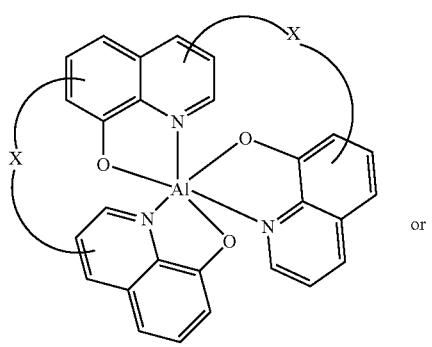

-continued

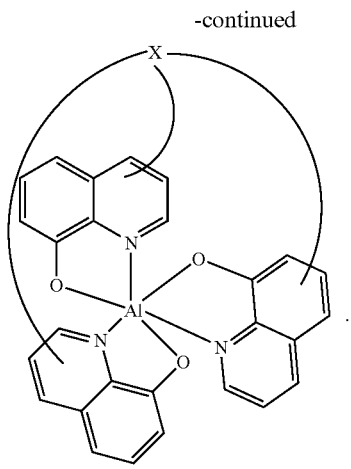

In another embodiment of the invention, one or more linking groups X link two bidentate ligands Q and one monodentate ligand J to give a pentadentate ligand system that may be represented by the formula XIV$_a$, XIV$_b$ and XIV$_c$

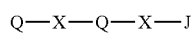 (XIV$_a$)

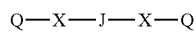 (XIV$_b$)

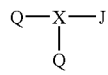 (XIV$_c$)

wherein each X is independently selected form a linking group, and each bidentate ligand Q may be the same or may be different. The linking group(s), X, may be connected to each bidentate ligand Q or monodentate ligand J by a covalent bond to any carbon or heteroatom of the ligand that does not interfere with the ligand's ability to bind to the Al and form a pentadentate system. Examples of the case where the pentadentate ligand system is comprised of two 8-hydroxy-quinolinato ligands linked by a linking group(s), X, to a 4-phenylphenolate ligand are depicted below:

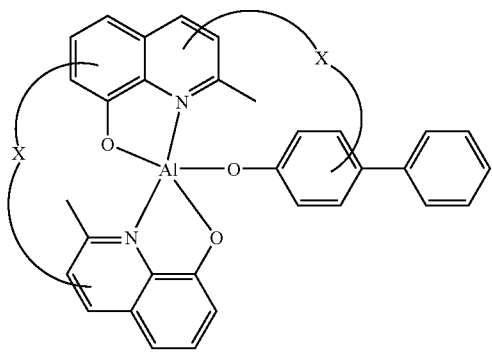

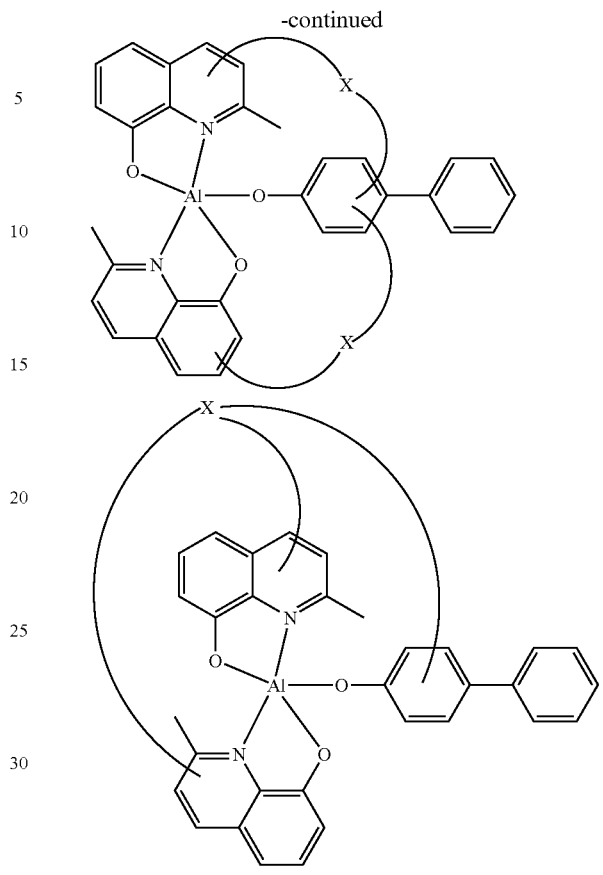

The compounds of invention may be prepared by methods known in the art. In preferred embodiments, the multidentate ligand systems are prepared by the metal catalyzed coupling of the linking group to the ligand. See, for example, Beeston et al., Inorg. Chem. 1998, 37, 4368-4379. Metal complexes of the formula VII may be prepared, for example, according to the synthesis provided in Scheme I:

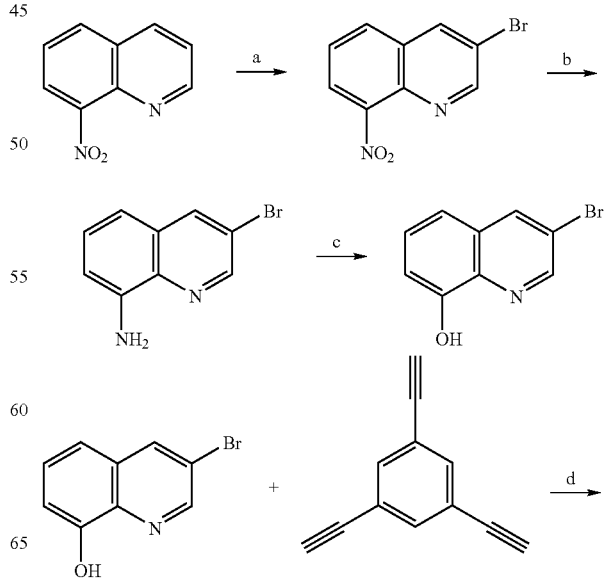

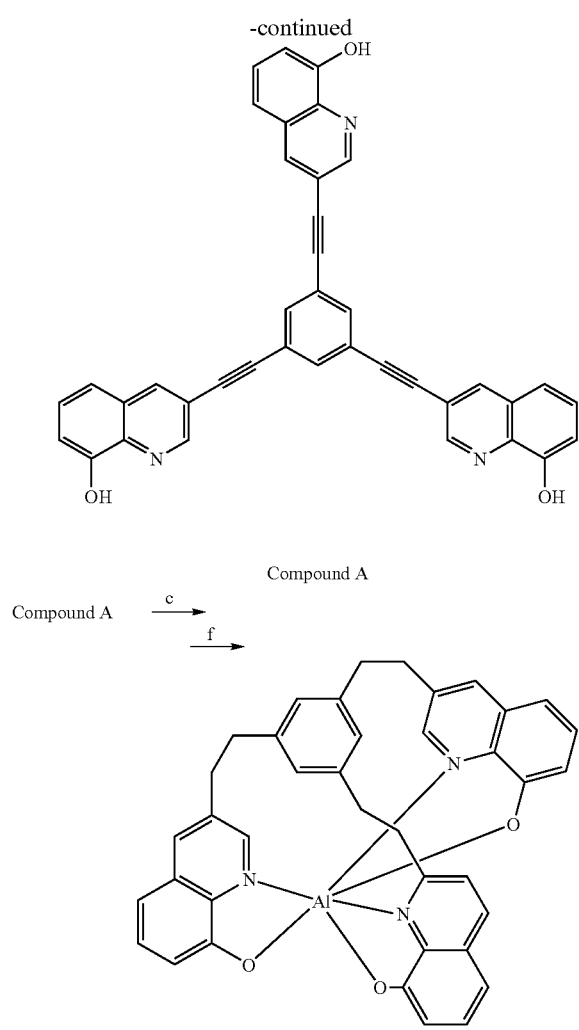

Compound A

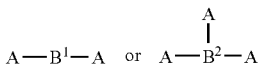

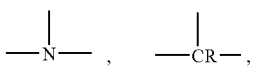

Scheme 1: a) NBS, acetic acid; b) Fe, HCl, ethanol c) H$_2$SO$_4$, H$_2$O, 220° C.; d) Pd(PPh3)$_4$, CuI, diisopropyl amine, toluene, 60° C. e) cyclohexene, Pd 10% on Carbon, THF; f) aluminum isopropoxide, toluene.

The materials of the present invention comprise one or more linking groups, X, that links together two or more ligands (L, Q, or J). The linking group, X, may be connected to a ligand by a covalent bond to any carbon or heteroatom of the ligand that does not interfere with the ligands ability to bind to the metal. The linking group may be any group that is covalently bound to two or more of the ligands, and which does not interfere with the ligand's individual abilities to bind to the same metal. Linking groups may include, for example, organic, organometallic and other metal containing groups. Representative groups suitable for use as a linking group are bivalent and trivalent alkyl groups, aryl groups, silanes, ethers, and polyethers.

The ligands connected by the linking group X may be the same or different. For example the linking group, X, may link two tridentate ligands or three bidentate ligands or a bidentate and a tetradentate ligand to form a hexadentate ligand system. In one preferred embodiment, three bidentate ligands are joined by a common linking group X. In another embodiment, three bidentate ligands are each independently connected to a first linking group and a second linking group wherein the first and the second linking group may be the same or different.

In a preferred embodiment, the linking group X provides no π-conjugation between the linked ligands. Having π-conjugation between the linked ligands may change the electronic properties of the ligands and the resulting metal complexes, such as a red-shift in the luminescence. It is desirable to link the ligands together to without significantly altering the electronic properties of the ligands and the resulting metal complex. A non-conjugated linking group may comprise at least one atom in the linkage which contains no π-electrons, such as an sp$^3$ hybridized carbon or silicon.

In one preferred embodiment, the linking group, X, is connected by a covalent bond to a phenyl moiety in a first ligand and links the first ligand to at least a second ligand via a covalent bond to a phenyl moiety in the second ligand. In a more preferred embodiment, three ligands are linked together by a linking group covalently bound to a phenyl moiety on each ligand.

In an alternative embodiment, X is connected by a covalent bond to a pyridyl moiety of a first ligand and connects the first ligand to at least a second ligand via a covalent bond to a pyridyl moiety on the second ligand. In a preferred alternative embodiment, three ligands are linked together by a linking group covalently bound to a pyridyl moiety on each ligand.

In a preferred embodiment of the invention, the linking group, X, is selected from the group consisting of —(CR$_2$)$_d$—, —[O(CR$_2$)$_e$]O—, or a group having the formula $$A-B^1-A \quad \text{or} \quad A-\underset{\underset{A}{|}}{B^2}-A$$

wherein
A is —(CR$_2$)$_f$—, or -Z-(CR$_2$)$_g$—;
Z is —O—, —NR—, or —SiR$_2$—;
B$^1$ is —O—, —NR—, —CR=CR—, aryl, heteroaryl, cycloalkyl, or a heterocyclic group,
B$^2$ is $$-\underset{|}{N}- \, , \quad -\underset{|}{CR}- ,$$

alkyl, aryl, heteroaryl, cycloalkyl, or a heterocyclic group;
each R is independently selected from H, alkyl, aralkyl, aryl and heteroaryl,
d is 1 to 6,
e is 1 to 6,
f is 1 to 4, and
g is 1 to 4.

It is believed that the metal complexes with multidentate ligands may have improved chemical, thermochemical, electrochemical and photochemical stability compared to the traditional bidentate ligand analogs. As would be understood by those of skill in the art, the improvement in stability may be attributed, at least in part, to what is known as the "chelate effect" such as described in *Inorganic Chemistry* (2nd Edition), Gary L. Miessler, Donald A. Tarr (Prentice Hall, 1998) pp 396-397. Linking two or more ligands to one another may render the resulting ligand system less labile than the corresponding non-linked ligands. As indicated in the mass spectroscopy (EI, 70 eV) of Dopant F (described herein below), for example, there is no fragmentation of the molecular ion whereas significant fragmentation is observed in Ir(Ppy)$_3$.

It is believed that the metal complexes with multidentate ligands can have increased photoluminescence quantum yields compared to the traditional bidentate ligand analogs because the complexes with multidentate ligands are more rigid, i.e., with decreased vibrational and rotational freedom, which can be pathways for non-radiative decay.

In metal-ligand complexes, structural isomers may result from the synthesis. For example, in Ir(phenylpyridine)$_3$ type complexes, both facial and meridional isomers can form. Separation of these isomers may be difficult. Through suitable interlinking of the ligands, selective structural isomeric configuration can be achieved. For example, in Dopant F, as the ligands are interlinked through the pyridine rings, the only structural isomer possible is the facial isomer. Similarly, in Dopant M (also described herein below), as the ligands are interlinked through the phenyl rings, the only structural isomer possible is the facial isomer. This can significantly improve the synthesis yield and simplify the purification process.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, CO$_2$R, C(O)R, NR$_2$, cyclic-amino, NO$_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, CO$_2$R, C(O)R, NR$_2$, cyclic-amino, NO$_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, CO$_2$R, C(O)R, NR$_2$, cyclic-amino, NO$_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, CO$_2$R, C(O)R, NR$_2$, cyclic-amino, NO$_2$, and OR.

The term "aralkyl" as used herein contemplates an alkyl group which has as a substituent an aromatic group. Additionally, the aralkyl group may be optionally substituted on the aryl with one or more substituents selected from halo, CN, CO$_2$R, C(O)R, NR$_2$, cyclic-amino, NO$_2$, and OR.

The term "heterocyclic group" as used herein contemplates non-aromatic cyclic radicals. Preferred heterocyclic groups are those containing 5 or 6 ring atoms which includes at least one hetero atom, and includes cyclic amines such as morpholino, piperdino, pyrrolidino, and the like, and cyclic ethers, such as tetrahydrofuran, tetrahydroyran, and the like.

The term "aryl" or "aromatic group" as used herein contemplates single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

All value ranges, for example those given for n and m, are inclusive over the entire range. Thus, for example, a range of 0 to 4 would include the values 0, 1, 2, 3 and 4.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

—Material Definitions:

As used herein, abbreviations refer to materials as follows:
CBP: 4,4'-N,N-dicarbazolebiphenyl
m-MTDATA 4,4',4"-tris(3-methylphenylphenlyamino)triphenylamine
Alq$_3$: 8-tris-hydroxyquinoline aluminum
Bphen: 4,7-diphenyl-1,10-phenanthroline
n-BPhen: n-doped BPhen (doped with lithium)
F$_4$-TCNQ:tetrafluoro-tetracyano-quinodimethane
p-MTDATA: p-doped m-MTDATA (doped with F$_4$-TCNQ)
Ir(ppy)$_3$: tris(2-phenylpyridine)-iridium
Ir(ppz)$_3$: tris(1-phenylpyrazoloto,N,C(2')iridium(III)
BCP: 2,9-dimethyl-4,7-diphenyl-1,10-phenanthroline
TAZ: 3-phenyl-4-(1'-naphthyl)-5-phenyl-1,2,4-triazole
CuPc: copper phthalocyanine
ITO: indium tin oxide
NPD: N,N'-diphenyl-N-N'-di(1-naphthyl)-benzidine
TPD: N,N'-diphenyl-N-N'-di(3-toly)-benzidine
BAlq: aluminum(III)bis(2-methyl-8-hydroxyquinolinato)4-phenylphenolate
mCP: 1,3-N,N-dicarbazole-benzene
DCM: 4-(dicyanoethylene)-6-(4-dimethylaminostyryl-2-methyl)-4H-pyran
DMQA: N,N'-dimethylquinacridone
PEDOT:PSS: an aqueous dispersion of poly(3,4-ethylenedioxythiophene) with polystyrenesulfonate (PSS)
Ir(4,6-F$_2$PPY)$_3$: tris[2-(4,6-difluorophenyl)pyridine]iridium (III)
mCP: 3,5-N,N'-dicarbazolebenzene Experimental:

Specific representative embodiments of the invention will now be described, including how such embodiments may be made. It is understood that the specific methods, materials, conditions, process parameters, apparatus and the like do not necessarily limit the scope of the invention.

Where available, solvents and reagents were purchased from Aldrich Chemical Company. The reagents were of the highest purity and used as received.

mCP was prepared by the palladium-catalyzed cross coupling of aryl halides and arylamines. (T. Yamamoto, M. Nishiyama, Y. Koie *Tet. Lett.*, 1998, 39, 2367-2370).

EXAMPLE 1

Synthesis of Dopant F

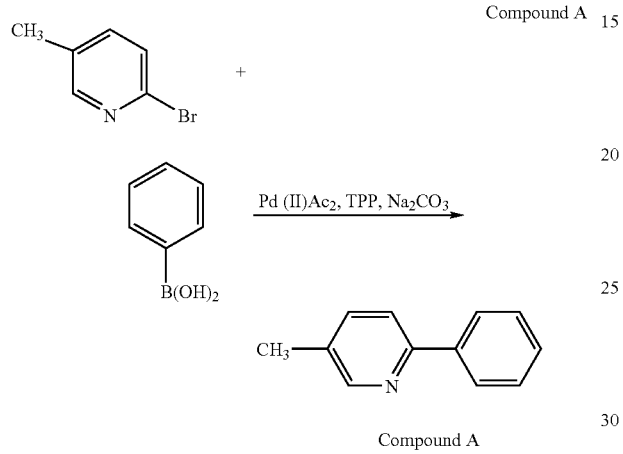

Compound A

Approximately 300 mL of 1,2-dimethoxyethane and 150 mL of distilled water were added to a 1000 mL round bottom flask. To this mixture 250 g of 2-bromo-5-methyl pyridine, 17.7 g of phenylboronic acid, 0.81 g of palladium (II) acetate, 3.8 g of triphenylphosphine, and 41.5 g of sodium carbonate were added. This mixture was heated to reflux under nitrogen atmosphere for 16 hours. After the reaction was cooled, 200 mL water and 150 mL ethyl acetate were added. The mixture was added to a separatory funnel and the organic and aqueous layers were allowed to separate. The organic layer was then washed with brine and dried over magnesium sulfate. After removal of the solvents by rotary evaporation, the crude mixture was purified by silica gel column chromatography using 10% EtOAc/Hexanes as the eluent. The fractions containing the desired product were combined and solvent was removed by rotary evaporation. About 100 mL of hexane was added to the obtained oil and cooled in ice water after which crystallization occurred. The crystals were isolated by vacuum filtration. Fifteen grams of white solid was obtained.

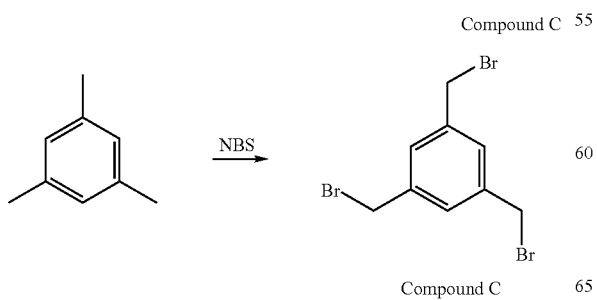

Compound C

A mixture of 500 mL of methyl formate, 20.4 g of mesitylene, 100 grams of n-bromosuccimide, and 0.2 g of 2,2'-azobisisobutyronitrile were added to a 1000 mL round bottom flask. This mixture was heated to reflux for 16 hours and then extracted with a saturated solution of sodium bicarbonate twice. The organic layer was then dried over magnesium sulfate and the solvent removed by rotary evaporation. About 300 mL of hexane was added to the resulting oil and heated to reflux until a clear solution was obtained. Cooling to room temperature caused the formation of white crystals that were then vacuum filtered. This crystallization technique was repeated twice more to yield 7 g of white solid.

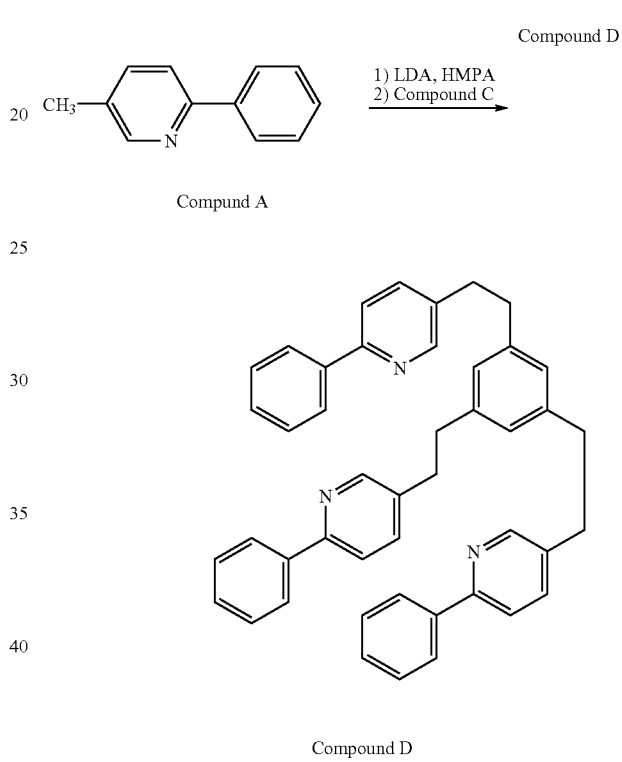

Compound D

To an oven dried 250 mL round bottom flask, 20 mL of dry tetrahydrofuran and 4.18 g of diisopropylamine were added. This mixture was cooled in an ice bath and 25.9 mL of 1.6M n-butyl lithium was added drop wise. The mixture was stirred for 30 minutes and then 7.41 g of hexamethylphosphoramide was added drop wise. After stirring for 30 minutes, 7.0 g of compound A in 15 mL of dry tetrahydrofuran was added drop wise. This mixture was allowed to stir at room temperature for 18 hours. After cooling in a dry ice/acetone bath, 1.85 g of compound C in 15 mL of dry tetrahydrofuran was added drop wise. After stirring for 1 hour the reaction was quenched with water and extracted with ethyl acetate. The organic layer was washed with brine and then dried over magnesium sulfate. Removal of the solvent by rotary evaporation resulted in a brown oil which was purified by silica gel column chromatography using 40% EtOAc/hexanes as the eluent. The fractions containing the desired product were combined and the solvent removed to yield 1 gram of yellow oil.

EXAMPLE 2

Synthesis of Dopant G

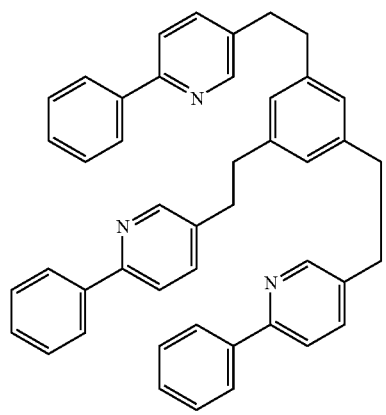

Dopant F

+ IrCl₃ +

AgOCOCF₃ →

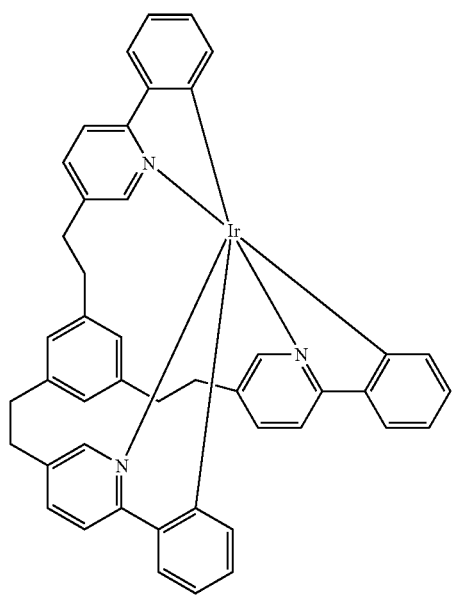

Dopant F

To a 250 mL round bottom flask 40 mL 1,2-dichlorobenzene, 2 mL water, 0.9 g of compound D, 0.52 g of IrCl₃, and 1.28 g of silver trifluoroacetate were added. This mixture was heated to reflux under nitrogen for 4 hours. After cooling to room temperature, the reaction mixture was passed through a silica gel plug with 50% CH₂Cl₂/hexanes as the solvent system. The good fractions were combined and the solvent was removed. Yellow crystals were collected from a dichloromethane/methanol mixture. The product was further purified by sublimation. The desired product was confirmed by mass spectroscopy and $^1$H NMR. $\lambda_{max}$ (emission) of the compound was 508 nm in dichloromethane.

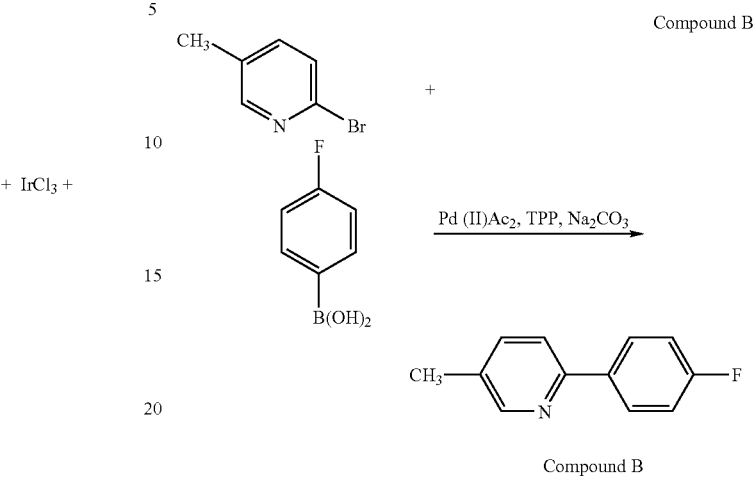

Compound B

Approximately 250 mL of 1,2-dimethoxyethane and 100 mL of distilled water were added to a 1000 mL round bottom flask. To this mixture 15.0 g of 2-bromo-5-methyl pyridine, 12.2 g of 4-fluorophenylboronic acid, 0.48 g of palladium (II) acetate, 2.3 g of triphenylphosphine and 23.0 g of sodium carbonate were added. This mixture was heated to reflux under nitrogen atmosphere for 16 hours. After the reaction was cooled, 150 mL water and 150 mL ethyl acetate were added. The mixture was added to a separatory funnel and the organic and aqueous layers were allowed to separate. The organic layer was then washed with brine and dried over magnesium sulfate. After removal of the solvents by rotary evaporation, the crude mixture was purified by silica gel column chromatography using 10% EtOAc/hexanes as the eluent. The fractions containing the desired product were combined and the solvent was removed by rotary evaporation. About 100 mL of hexane was added to the obtained oil and cooled in ice water after which crystallization occurred. The crystals were isolated by vacuum filtration. Ten grams of white solid was obtained.

Compound E

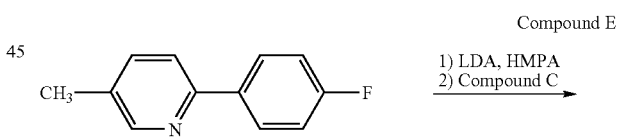

Compound B

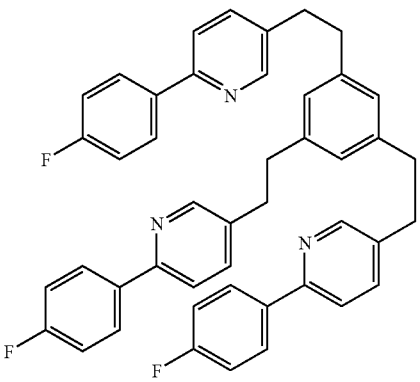

Compound E

To an oven dried 100 mL round bottom flask 10 mL of dry tetrahydrofuran and 0.54 g of diisopropylamine were added. This mixture was cooled in an ice bath and 3.3 mL of 1.6 M n-butyl lithium was added drop wise. The mixture was stirred for 30 minutes and then 0.95 g of hexamethylphosphoramide were added drop wise. After stirring for 30 minutes, the reaction mixture was cooled to −78° C. and then 1.0 g of compound B in 10 mL of dry tetrahydrofuran was added drop wise. After stirring for 4 hours at −78° C., 1.85 g of compound C in 15 mL of dry tetrahydrofuran was added drop wise. After stirring for 1 hour the reaction was quenched with water and extracted with ethyl acetate. The organic layer was then washed with brine and dried over magnesium sulfate. Removal of the solvent by rotary evaporation resulted in a brown oil which was purified by silica get column chromatography using 30% EtOAc/hexanes as the eluent. The fractions containing the desired product were combined and the solvent removed to yield 0.3 grams of white solid.

To a 100 mL round flask, 15 mL 1,2-dichlorobenzene, 1 mL water, 0.1 g of compound E, 0.05 g of IrCl$_3$, and 0.13 g of silver trifluoroacetate were added. This mixture was heated to reflux under nitrogen for 5 hours. After cooling to room temperature the reaction mixture was passed through a silica gel plug with 50% MeCl$_2$/hexanes as the eluent. The desired fractions were combined and the solvent removed in vacuo. Yellow crystals were collected from a dichloromethane/methanol mixture. The desired product was confirmed by mass spectroscopy. Emission of the material in dichloromethane gave a $\lambda_{max}$ at 480 nm.

EXAMPLE 3

Synthesis of Dopant H

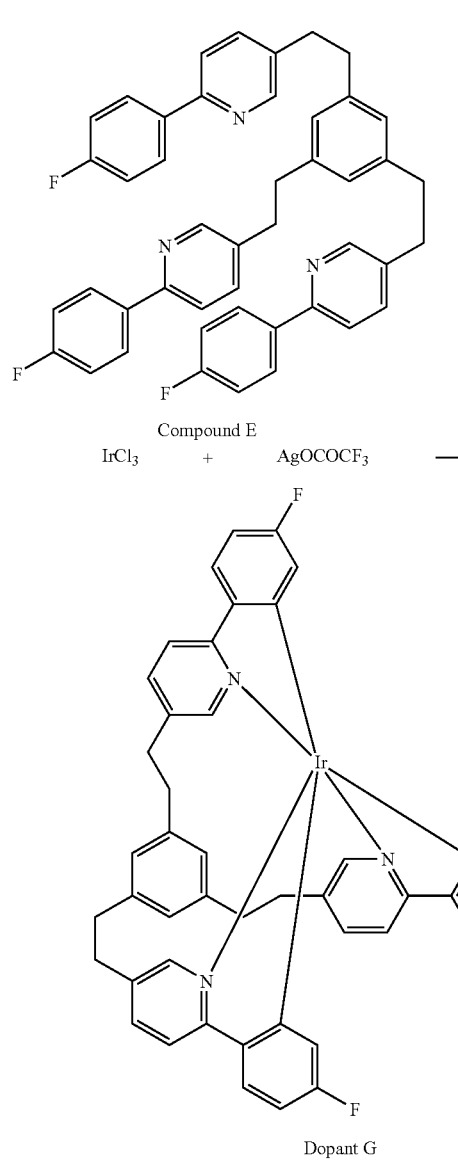

Dopant G

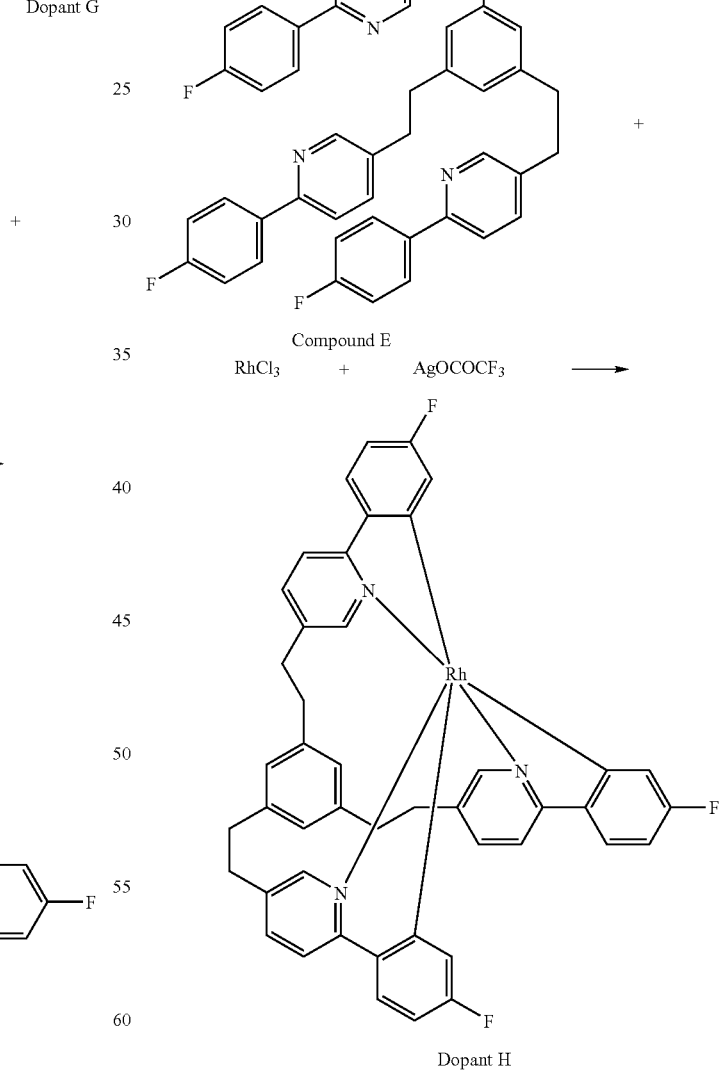

Dopant H

To a 100 mL round bottom flask 15 mL 1,2-dichlorobenzene, 1 mL water, 0.1 g of compound E, 0.04 g RhCl$_3$ g of silver trifluoroacetate were added. This mixture was heated to reflux under nitrogen for 5 hours. After cooling to room temp the reaction mixture was passed through a silica gel plug with 50% $CH_2Cl_2$/hexanes as the eluent. The desired fractions were combined and the solvent removed in vacuo. White crystals were collected from a dichloromethane/methanol mixture. The desired product was confirmed by mass spectroscopy. Emission of the material in dichloromethane gave a $\lambda_{max}$ at 456 nm.

EXAMPLE 4

Device Comparison

Device fabrication and measurement All devices are fabricated by high vacuum (<$10^{-7}$ Torr) thermal evaporation. The anode electrode is ~1200 Å of indium tin oxide (ITO). The cathode consists of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The current-voltage-luminance (IVL) characteristics and operational lifetime are measured and summarized in the Table 1. A typical display brightness level of 600 cd/$m^2$ for green emitting devices is chosen for the comparison between different devices.

TABLE 1

| Example | Phosphorescent Material | Efficiency (cd/A) at 600 cd/$m^2$ | % luminance retained at 1000 hrs (initial luminance) | Device CIE coordinates |
| --- | --- | --- | --- | --- |
| Linked Ligand | Dopant F | 25 | 91 (955 cd/$m^2$) | 0.29, 0.63 |
| Comparative example 1 (unlinked) | Ir(ppy)$_3$ | 23 | 89 (600 cd/$m^2$) | 0.30, 0.63 |

Linked Ligand Device

The organic stack consists of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 4.5, 6 or 9 wt % of Dopant F as the emissive layer (EML). The ETL2 is 100 Å of aluminum(III)bis(2-methyl-8-hydroxyquinolinato)4-phenylphenolate (BAlq). The ETL1 is 400 Å of tris(8-hydroxyquinolinato)aluminum (Alq$_3$).

COMPARATIVE EXAMPLE 1

The organic stack consists of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of 4,4'-bis(N-carbazolyl)biphenyl (CBP) doped with 6 wt % offac-tris(2-phenylpyridine)iridium [Ir(ppy)$_3$] as the emissive layer (EML). The ETL2 is 100 Å of aluminum(III)bis (2-methyl-8-quinolinato)4-phenylphenolate (BAlq). The ETL1 is 400 Å of tris(8-hydroxyquinolinato)aluminum (Alq$_3$).

Figure 3:
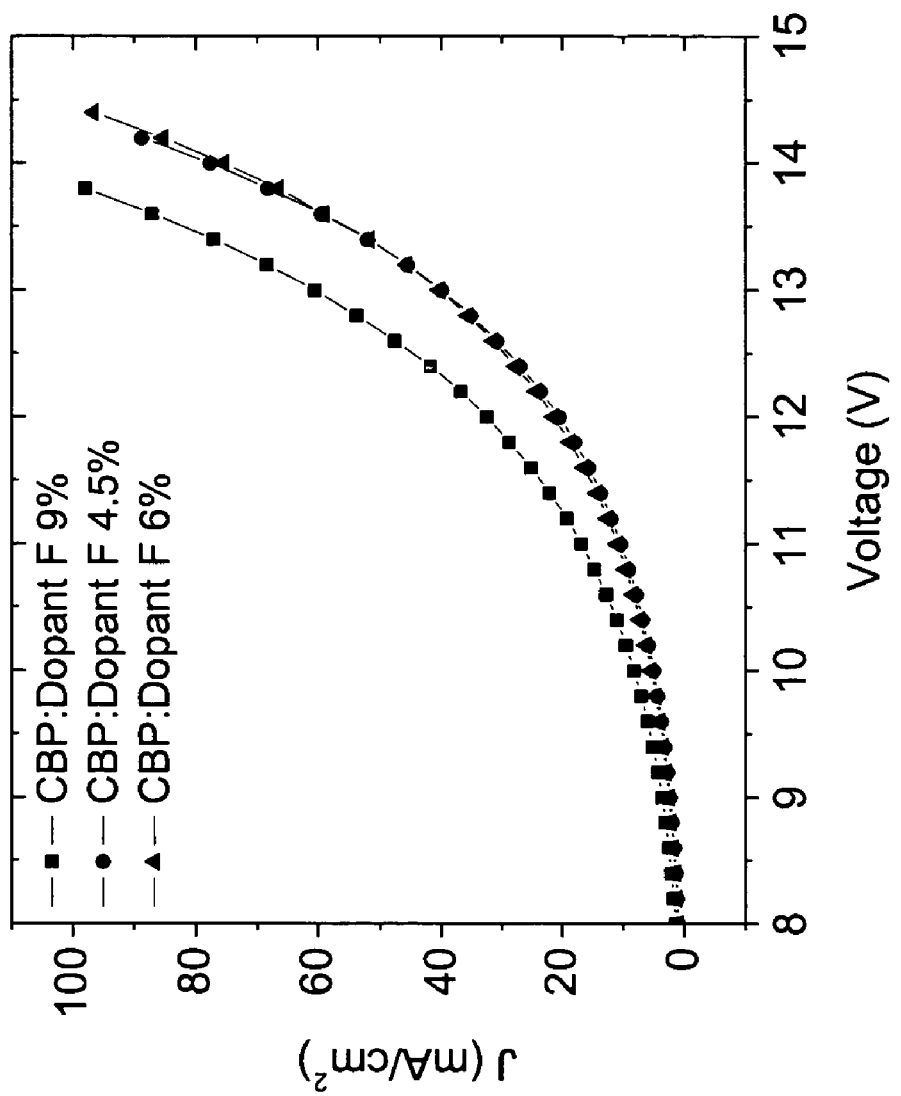
FIG. 3 shows the plot of current vs voltage for the device having the structure ITO/CuPc(100 Å)/NPD(300 Å)/CBP:dopant F/BAlq(100 Å)/Alq$_3$(400 Å)/LiF(10 Å)/Al(100 Å) in which the hexadentate emissive dopant, Dopant F, is doped into the CBP host at 4.5%, 6% and 9%.
Figure 4:
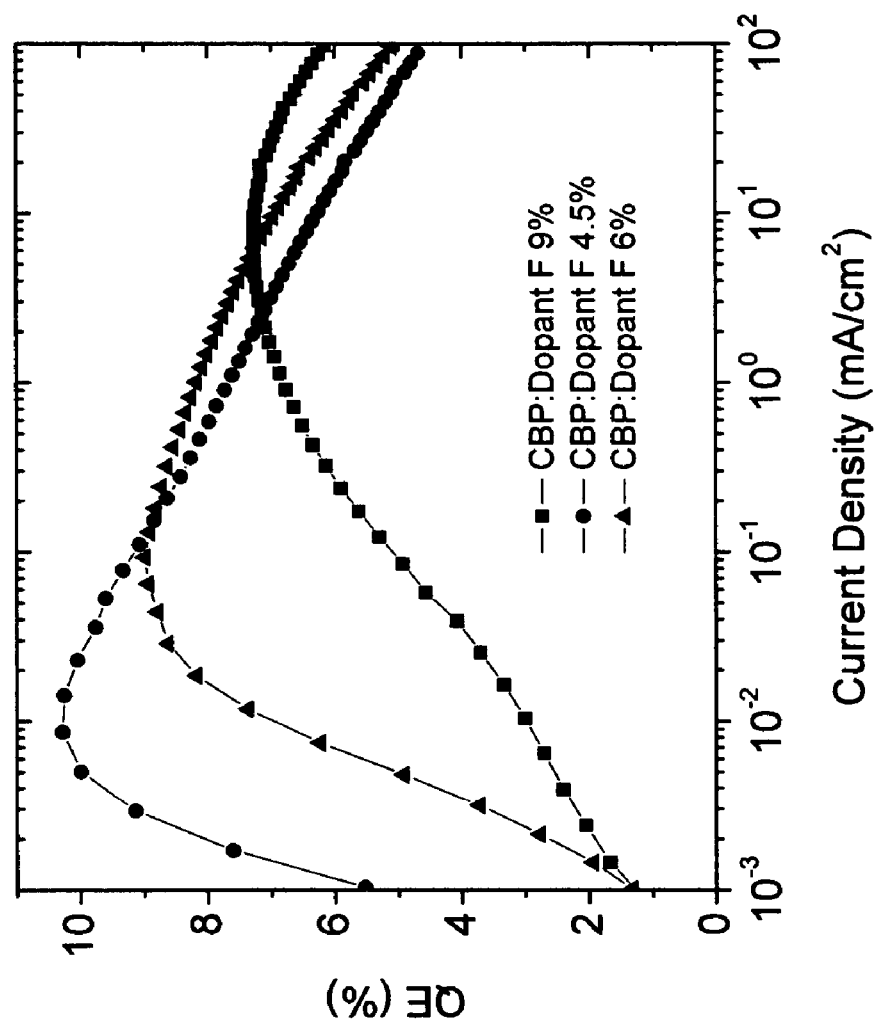
FIG. 4 shows the plot of external quantum efficiency vs current density for the device having the structure ITO/CuPc (100 Å)/NPD(300 Å)/CBP:dopant F/BAlq(100 Å)/Alq$_3$(400 Å)/LiF(10 Å)/Al(1000 Å) in which the hexadentate emissive dopant, Dopant F, is doped into the CBP host at 4.5%, 6% and 9%.
Figure 5:
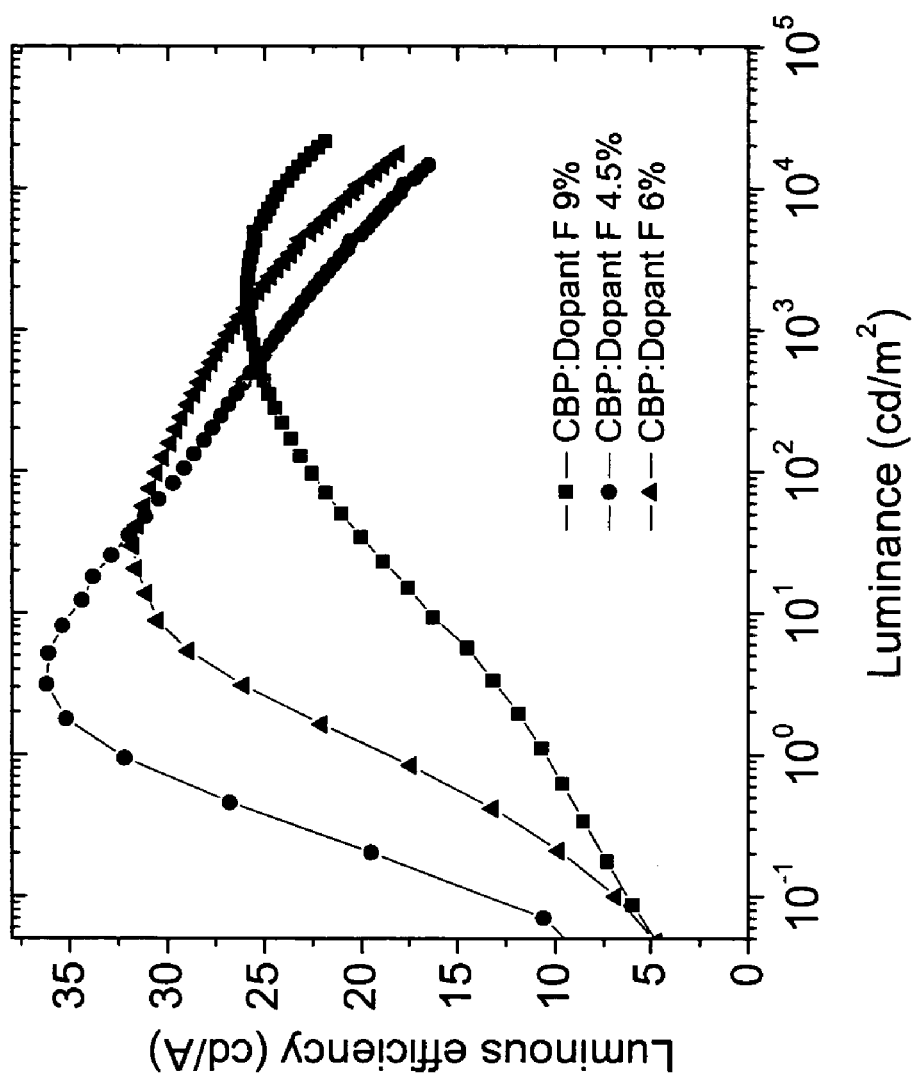
FIG. 5 shows the plot of luminous efficiency vs luminance for the device having the structure ITO/CuPc(100 Å)/NPD (300 Å)/CBP:dopant F/BAlq(100 Å)/Alq$_3$(400 Å)/LiF(10 Å)/Al(1000 Å) in which the hexadentate emissive dopant, Dopant F, is doped into the CBP host at 4.5%, 6% and 9%.
Figure 6:
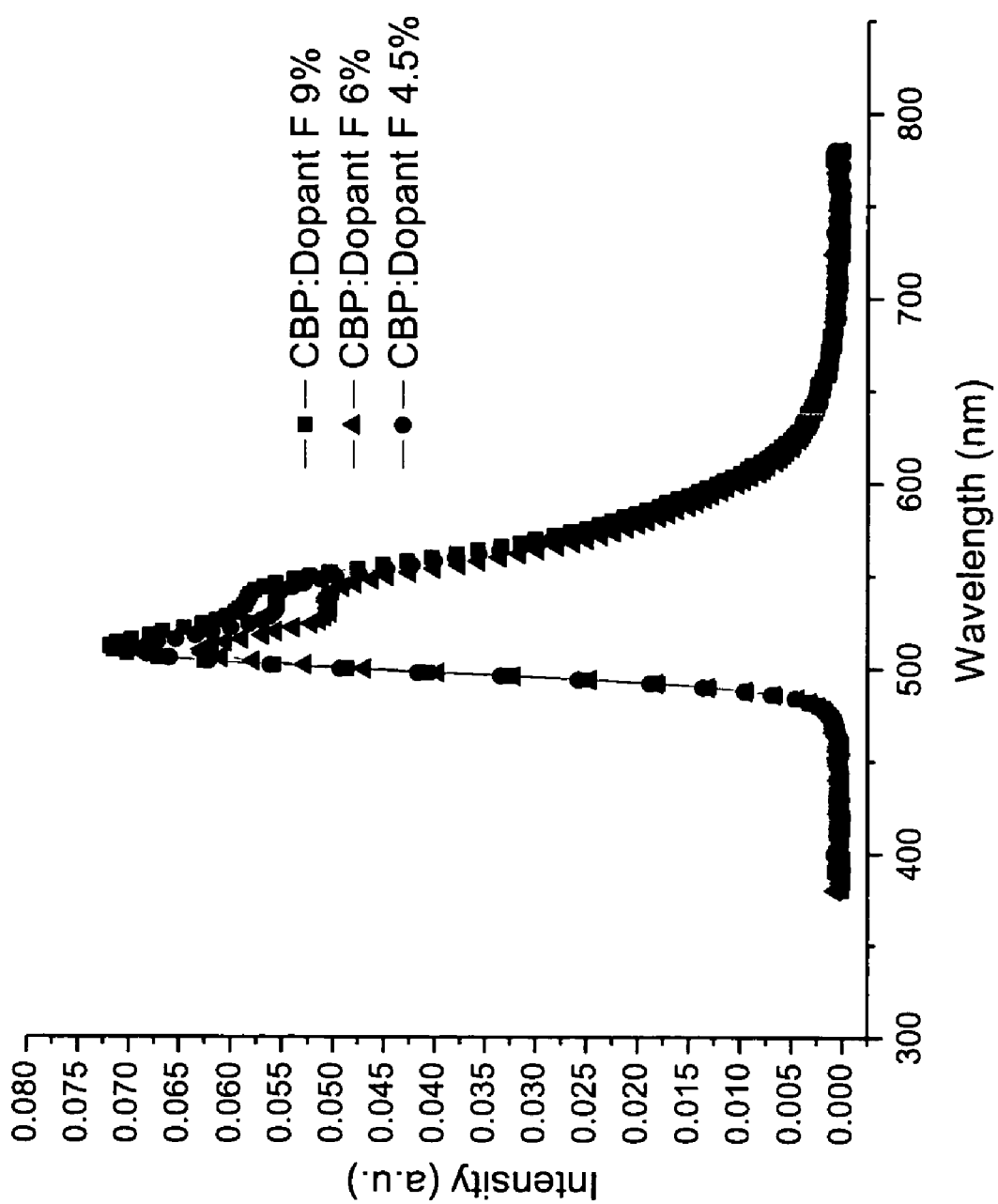
FIG. 6 shows the luminescent spectra for the devices having the structures (i) ITO/CuPc(100 Å)/NPD(300 Å)/CBP:dopant F (9%, 300 Å)/BAlq(100 Å)/Alq$_3$(400 Å)/LiF(10 Å)/ Al(1000 Å), (ii) ITO/CuPc(100 Å)/NPD(300 Å)/CBP:dopant F(4.5%, 300 Å)/BAlq(100 Å)/Alq(400 Å)/LiF(10 Å)/Al(1000 Å), and (iii) ITO/CuPc(100 Å)/NPD (300 Å)/CBP:dopant F(6%,300 Å)/BAlq(100 Å)/Alq(400 Å)/LiF(10 Å)/Al(1000 Å).

The linked ligand devices of Example 4 were characterized. The device characteristics are shown in FIGS. 3-6. The plot of current density vs voltage is shown in FIG. 3. FIG. 4 shows the plot of the external quantum efficiency at various current densities for these devices. FIG. 5 shows the plots of luminous efficiency for these devices. The devices show high quantum efficiency and luminous efficiencies. The device having a dopant concentration of 4.5% gave a maximum quantum efficiency of 10% and a maximum luminous efficiency of 36 cd/A. FIG. 6 shows the luminescent spectra for the device having dopant concentration of 4.5%, 6% and 9%.

Figure 7:
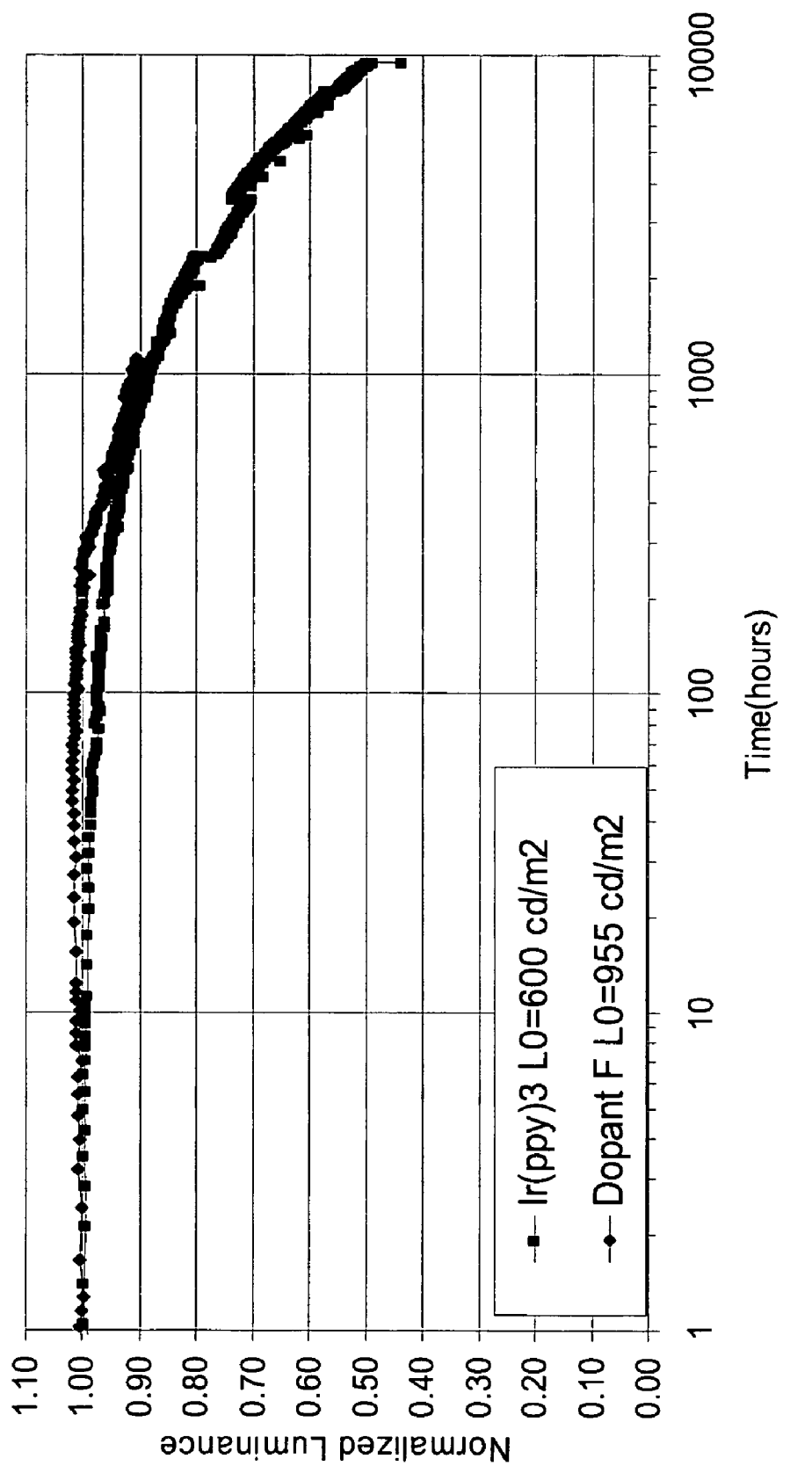
FIG. 7 shows the normalized luminance vs time for the devices having the structures ITO/CuPc(100 Å)/NPD(300 Å)/CBP:dopant F(4.5%, 300 Å)/BAlq(100 Å)/Alq(400 Å)/LiF(5 Å)/Al(1000 Å) and ITO/CuPc(100 Å)/NPD(300 Å)/CBP:Ir(ppy)$_3$(6%, 300 Å)/BAlq(100 Å)/Alq(400 Å)/LiF (10 Å)/Al(1000 Å).

The operational stability of the 4.5% doped linked ligand device was tested at room temperature under a constant direct current drive to achieve an initial luminance of 955 cd/M2. A comparison of stability was made to the comparative example 1 (unlinked ligand device) which was driven at a lower initial luminance of 600 cd/$M^2$ (FIG. 7). Without the enhanced stability provided by the present invention, one would have expected the device which was driven at higher initial luminance, to degrade more rapidly. The results indicate, however, that the linked ligands of the present invention exhibit enhanced stability since the linked ligand device of Example 4 degraded less than the unlinked ligand device (comparative Example 1) when operating at a 37% higher brightness. As shown, the linked ligand device utilizing Dopant F retains 91% of 955 cd/$m^2$ after 1000 hours of operation whereas comparative Example 1 utilizing unlinked Ir(ppy)$_3$ retains only 89% of 600 cd/$m^2$, after 1,000 hrs of continuous operation.

EXAMPLE 5

Synthesis of Dopant M

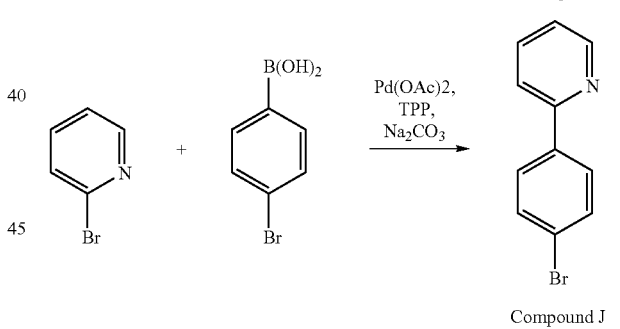

Compound J

Approximately 250 mL of 1,2-dimethoxyethane and 170 mL of a 2 M sodium carbonate solution were added to a 1000 mL round bottom flask. To this mixture, 39.0 g of 2-bromopyridine, 25.0 g of 4-bromophenylboronic acid, 0.70 g of palladium (II) acetate, and 3.26 g of triphenylphosphine were added. This mixture was heated to reflux under nitrogen atmosphere for 16 hours. After the reaction was cooled, 200 mL of water and 150 mL of ethyl acetate were added. The mixture was added to a separatory funnel and the organic and aqueous layers were allowed to separate. The organic layer was then washed with brine and dried over magnesium sulfate. After removal of the solvents by rotary evaporation, the crude mixture was purified by silica gel column chromatography using 10% EtOAc/Hexanes as the eluent. The fractions containing the desired product were combined and the solvent was removed by rotary evaporation. 22.0 g of white solid was obtained.

Compound K

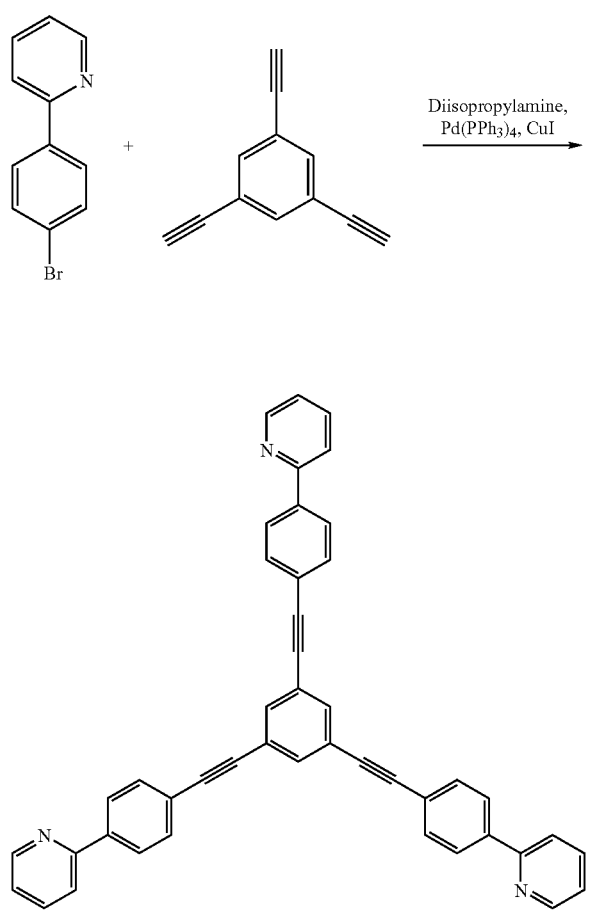

Compound K

Approximately 70 mL of dry toluene, 70 mL dry diisopropylamine, 10.0 g of Compound J, and 1.5 g of tetrakis(triphenylphosphine)palladium were added to a 500 mL round bottom flask. This mixture was heated to 60° C. for 30 minutes and then 2.14 g of 1,3,5 triethynylbenzene and 0.16 gr of copper(I) iodide were added. The reaction was maintained at 60° C. for 16 hours and then allowed to cool. The solids were filtered and the solvent was removed from the filtrate by rotary evaporation. The product was purified by silica gel column chromatography using 80% dichloromethane/ethyl acetate as the eluent. The fractions containing the desired product were combined and the solvent was removed by rotary evaporation. The product was crystallized from a dichloromethane/methanol mixture to yield 6 g of white needle crystals.

Compound K $\xrightarrow{\text{Cyclohexene, Pd on Carbon}}$ Compound L

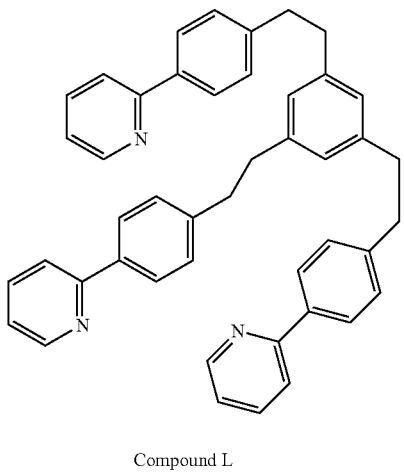

Compound L

Approximately 60 mL of cyclohexene, 60 mL of tetrahydrofuran, 3.0 g of 10% Pd on carbon, and 6 g of Compound K were added to a 250 mL round bottom flask. The reaction mixture was heated to reflux for 20 hours and then allowed to cool. The solids were removed by filtration and the solvent removed from the filtrate by rotary evaporation. The product was purified by silica gel column chromatography using 60% hexanes/ethyl acetate as the eluent. The fractions containing the desired product were combined and the solvent was removed by rotary evaporation. The pure product was crystallized from ethyl acetate/hexanes and filtered to yield 4.6 g of a white solid.

Compound L $\xrightarrow{\text{Ir(AcAc)}_3}$ Dopant M

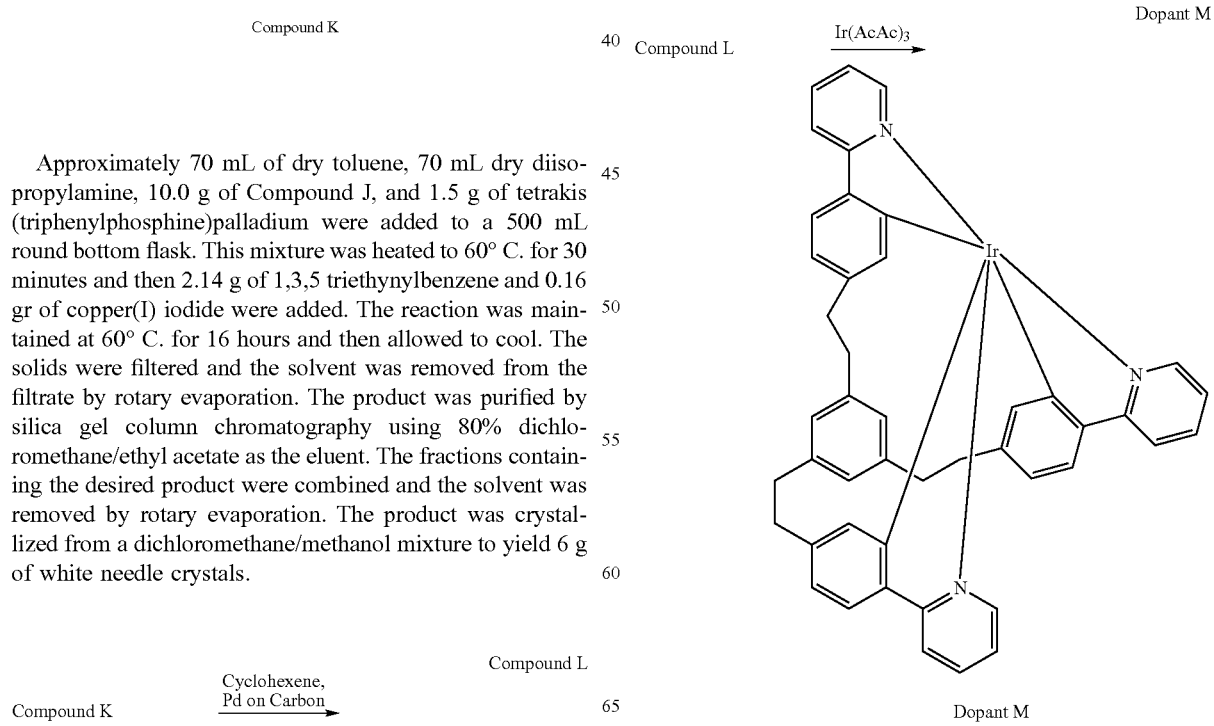

Dopant M

Approximately 200 mL of ethylene glycol, 1.85 g of Ir(AcAc)$_3$, and 2.5 g of compound L were added to a 500 mL round bottom flask. The reaction was heated to 160° C. under N$_2$ for 18 hours and then allowed to cool. Methanol was added and the yellow solids were filtered. These solids were dissolved in dichloromethane and filtered through a silica gel plug. The fractions containing the desired product were combined and the solvent was removed by rotary evaporation. The yellow solids were recrystallized from dichlormethane/methanol and filtered to yield 1.5 g of the desired product, which was characterized by mass spectroscopy and NMR. The product was further purified by sublimation.

EXAMPLE 6

Device Comparison

Figure 8:
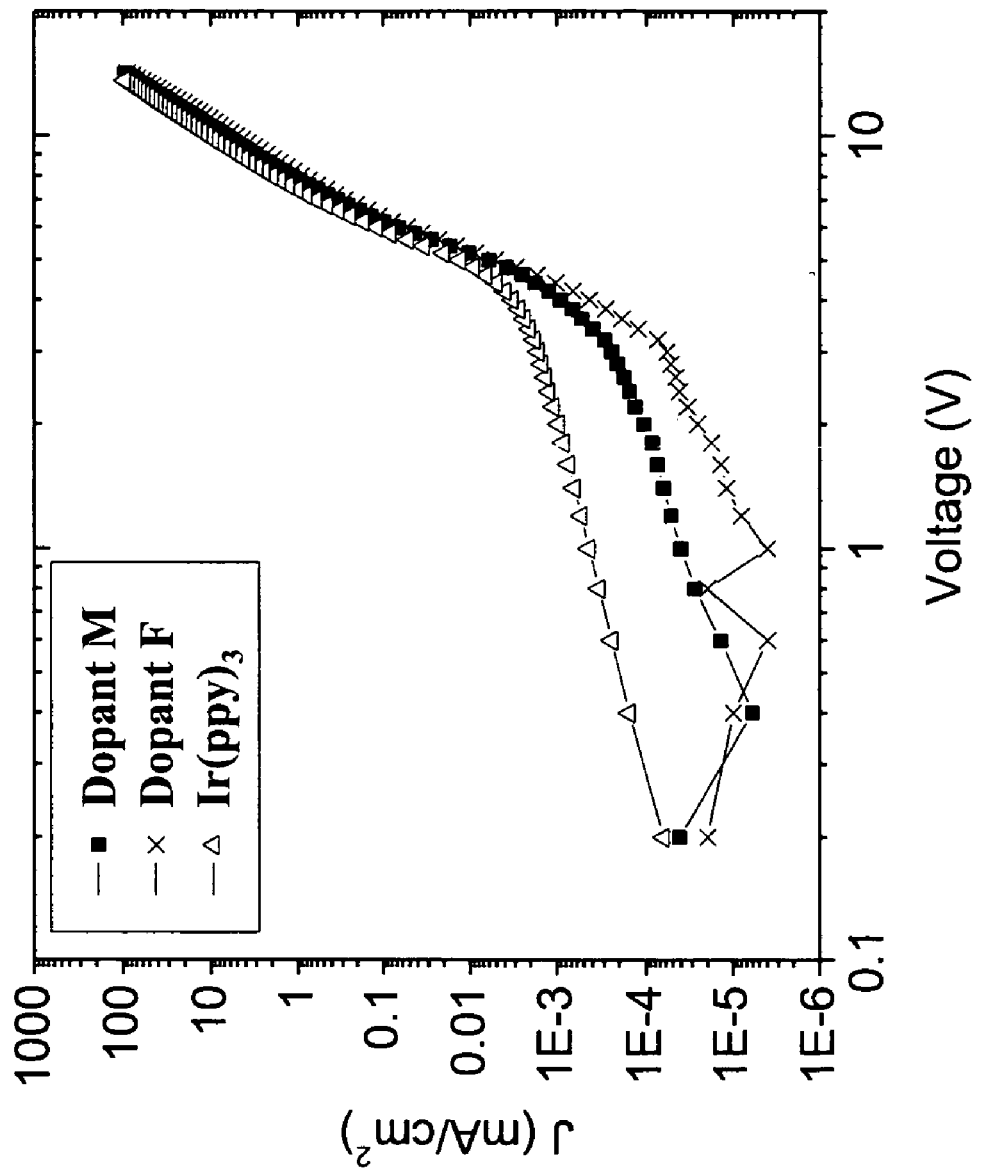
FIG. 8 shows the plot of current vs voltage(log scale) for devices having the structure ITO/CuPc(100 Å)/NPD(300 Å)/CBP:dopant (4.5%, 300 Å)/BAlq(100 Å)/Alq$_3$(400 Å)/LiF(10 Å)/Al(1000 Å) in which 2 hexadentate linked emissive dopants, Dopant F and Dopant M and unlinked dopant Ir(ppy)$_3$ doped into the CBP host at 4.5%, are compared.
Figure 9:
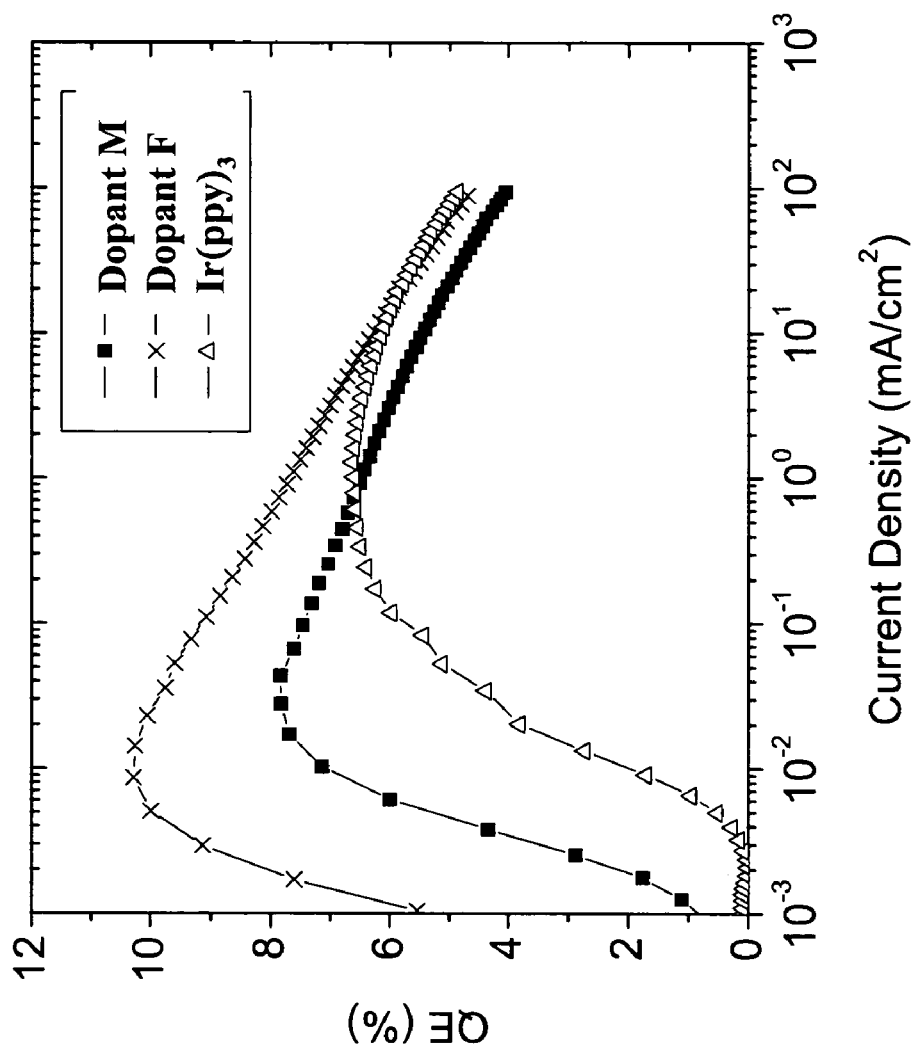
FIG. 9 shows the plot of external quantum efficiency vs current density for devices having the structure ITO/CuPc (100 Å)/NPD(300 Å)/CBP: dopant (4.5%, 300 Å)/BAlq(100 Å)/Alq$_3$(400 Å)/LiF(10 Å)/Al(1000 Å) in which 2 hexadentate linked emissive dopants, Dopant F and Dopant M and unlinked dopant Ir(ppy)$_3$ doped into the CBP host at 4.5%, are compared.
Figure 10:
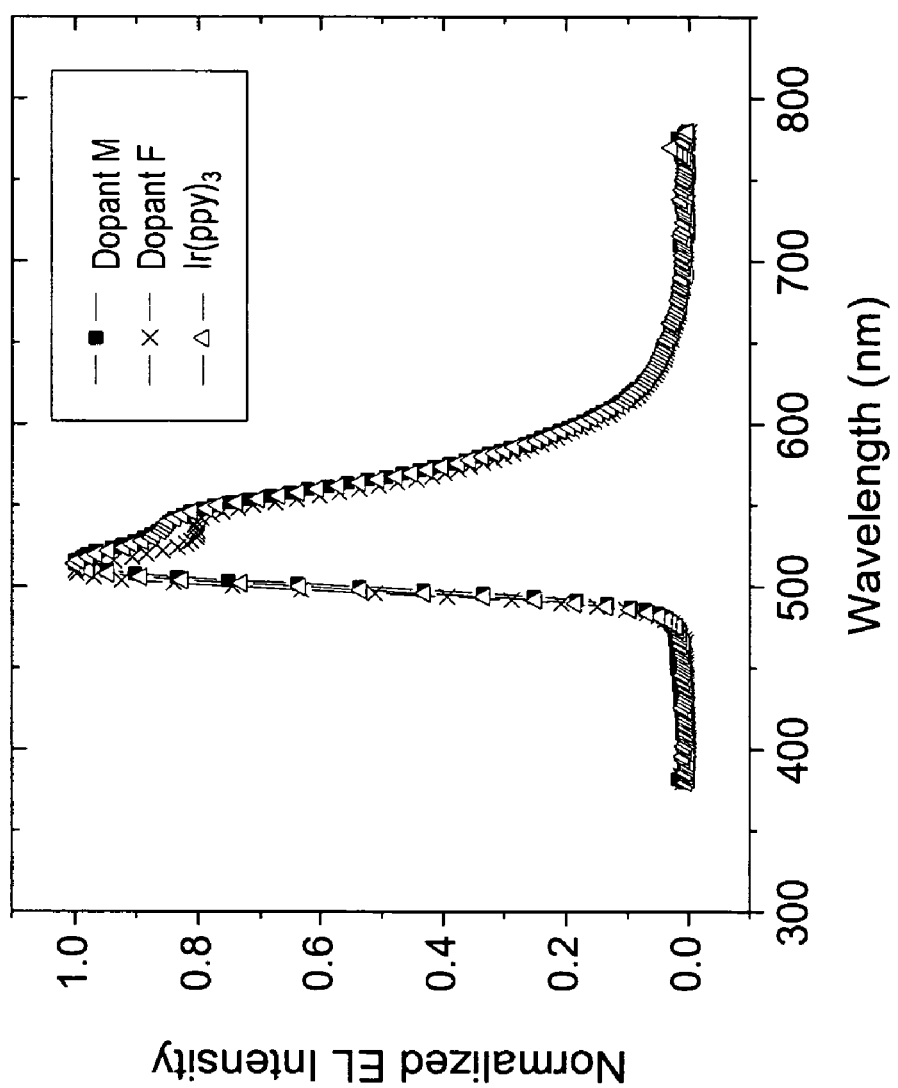
FIG. 10 shows the luminescent spectra for devices having the structures (i) ITO/CuPc(100 Å)/NPD(300 Å)/CBP:dopant F(4.5%, 300 Å)/BAlq(100 Å)/Alq$_3$(400 Å)/LiF(10 Å)/Al(1000 Å), (ii) ITO/CuPc(100 Å)/NPD(300 Å)/CBP:dopant M(4.5%, 300 Å)/BAlq(100 Å)/Alq$_3$(400 Å)/LiF(10 Å)/Al(1000 Å) and (iii) ITO/CuPc(100 Å)/NPD(300 Å)/CBP:Ir(ppy)$_3$ (4.5%, 300 Å)/BAlq(100 Å)/Alq$_3$(400 Å)/LiF(10 Å)/Al(1000 Å)

Linked hexadentate molecules, Dopant M and Dopant F and the analogous unlinked tris ligand Ir(ppy)$_3$ (Comparative Example 1) were compared as phosphorescent dopants in OLED devices. Devices were fabricated similarly to those in Example 4. The test device structure for each was ITO/CuPc(100 Å)/NPD(300 Å)/CBP:Dopant (4.5%, 300 Å)/BAlq(100 Å)/Alq$_3$(400 Å)/LiF(10 Å)/Al(1000 Å) where the dopant was Dopant F, Dopant M, or the unlinked analog ligand Ir(ppy)$_3$ (Comparative Example 1). A comparison of the device data for the three dopants is shown in FIGS. 8-10. The plot of current density vs voltage is shown in FIG. 8. FIG. 9 shows the plot of the external quantum efficiency as a function of current density for these devices. FIG. 10 shows the electroluminescent spectra for these devices. These devices were found to have high external quantum efficiency with emission characteristic of the dopant. All of these dopants have nearly identical green emission at ~510 nm. This demonstrates that the hexadentate linkage does not have a considerable effect on the color of emission.

Figure 11:
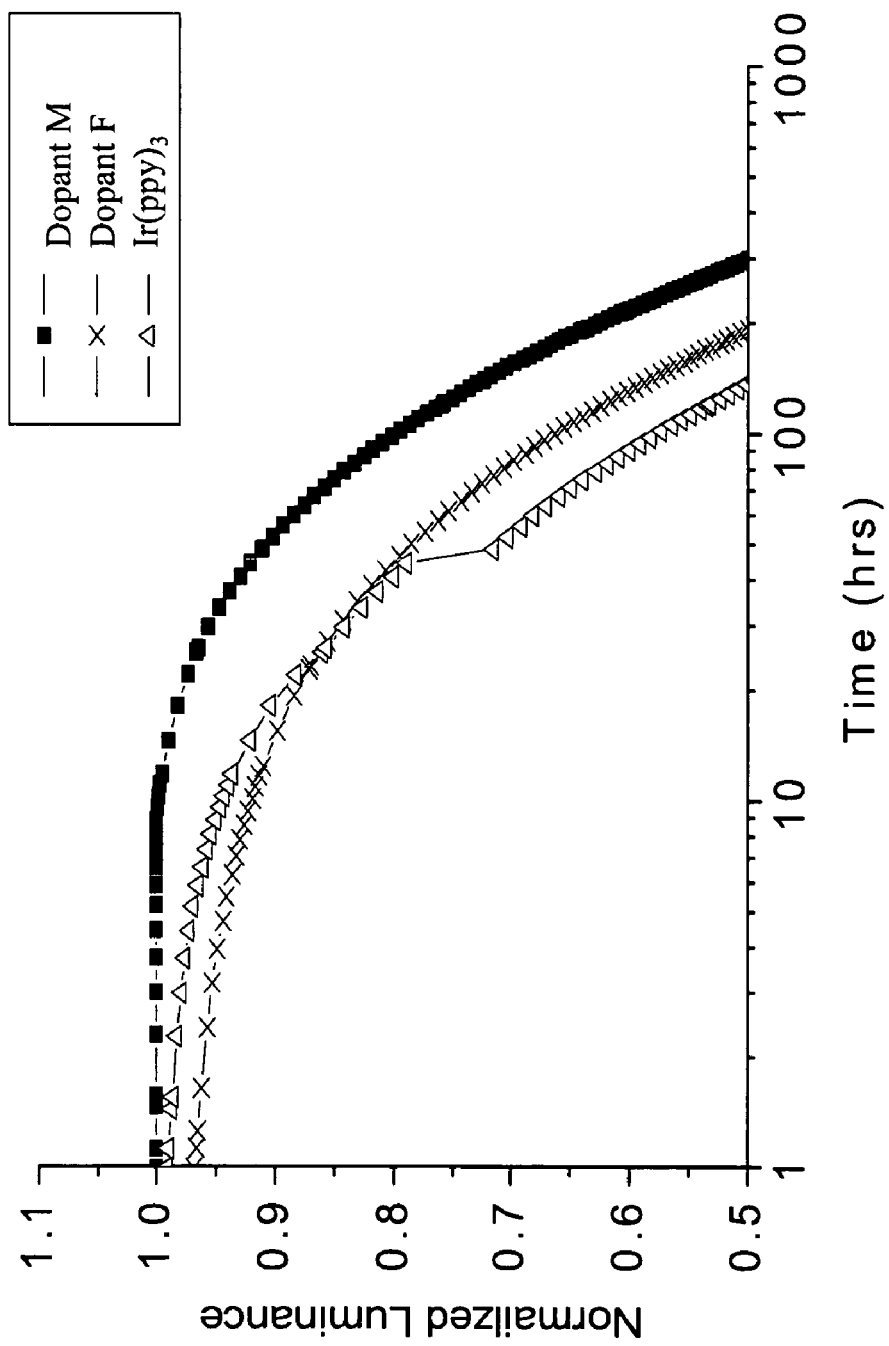
FIG. 11 shows the normalized luminance vs time for devices having the structure ITO/CuPc(100 Å)/NPD(300 Å)/CBP:dopant (4.5%, 300 Å)/BAlq(100 Å)/Alq$_3$(400 Å)/LiF(10 Å)/Al(1000 Å) in which 2 hexadentate linked emissive dopants, Dopant F and Dopant M and unlinked dopant Ir(ppy)$_3$ doped into the CBP host at 4.5%, are compared when driven at a constant current of 40 mA/cm$^2$.
Figure 12:
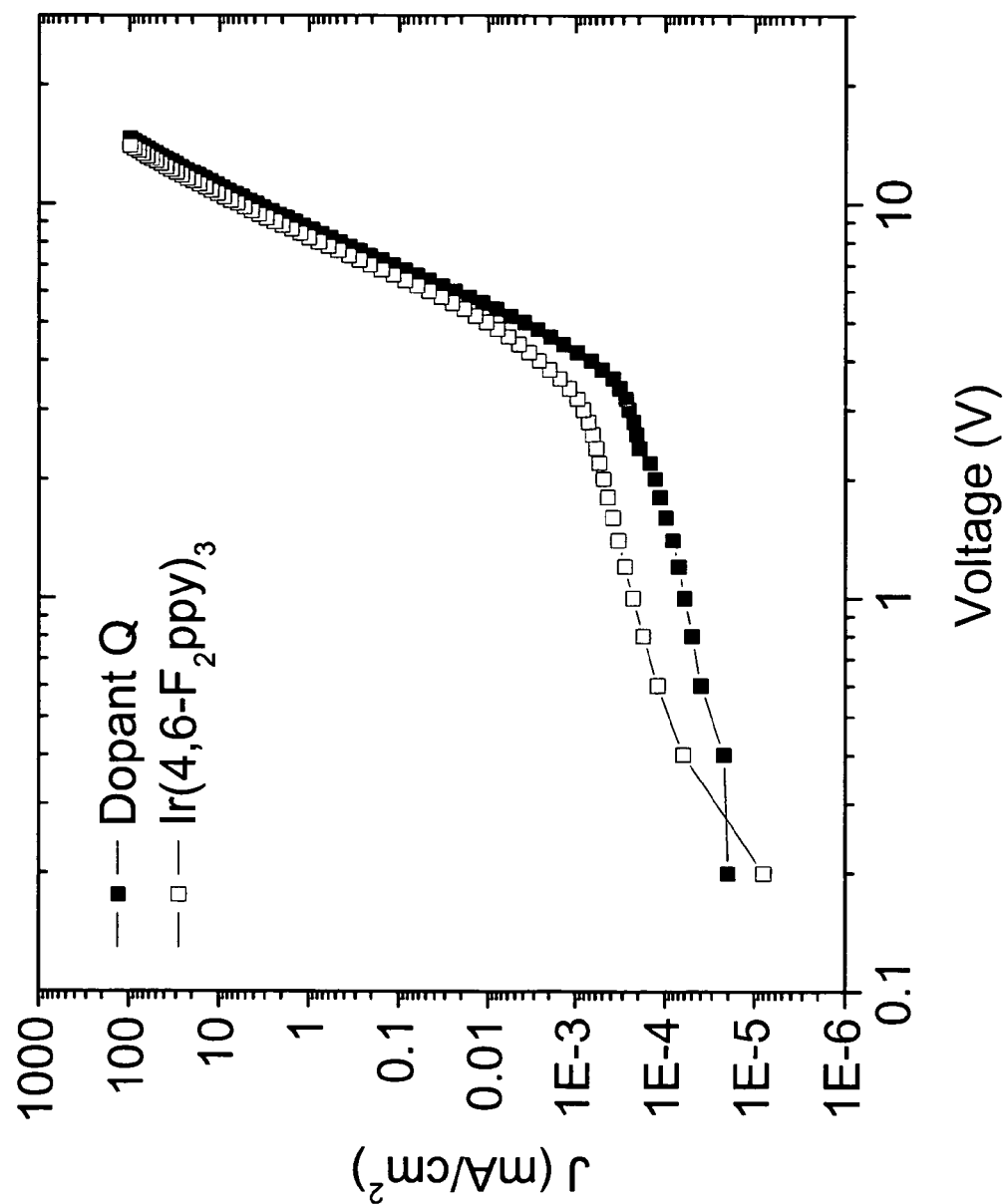
FIG. 12 shows the plot of current vs voltage(log scale) for devices having the structures ITO/CuPc(100 Å)/NPD(300 Å)/mCP:Dopant Q (6%, 300 Å)/BAlq(400 Å)/LiF(10 Å)/Al (1000 Å) and ITO/CuPc(100 Å)/NPD(300 Å)/mCP:Ir(4,6-F$_2$ppy)$_3$ (6%, 300 Å)/BAlq(400 Å)/LiF(10 Å)/Al(1000 Å).
Figure 13:
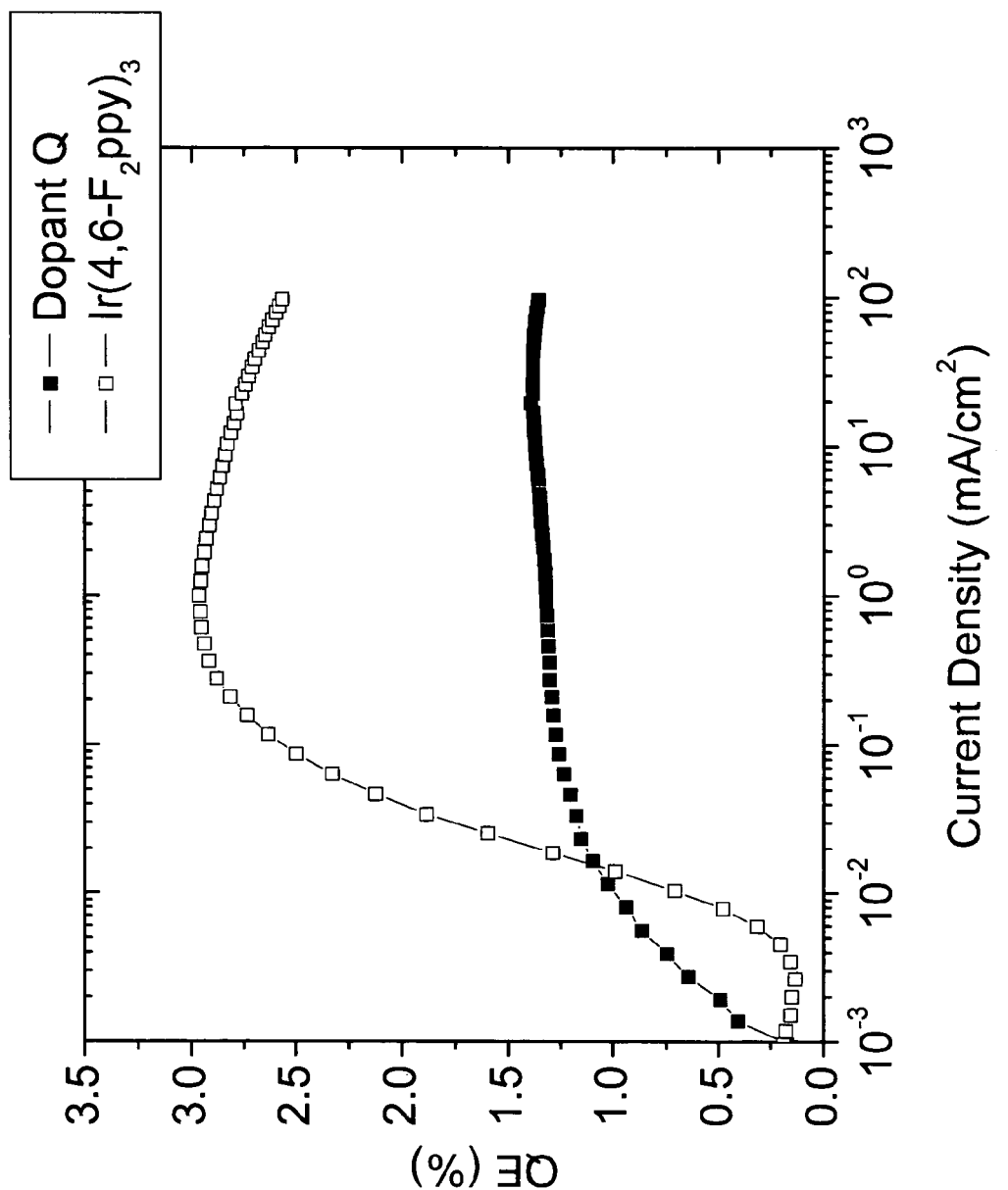
FIG. 13 shows the plot of external quantum efficiency vs current density for devices having the structures ITO/CuPc (100 Å)/NPD(300 Å)/mCP:Dopant Q (6%, 300 Å)/BAlq (400 Å)/LiF(10 Å)/Al(1000 Å) and ITO/CuPc(100 Å)/NPD (300 Å)/mCP:Ir(4,6-F$_2$ppy)$_3$ (6%, 300 Å)/BAlq(400 Å)/LiF (10 Å)/Al(1000 Å).
Figure 14:
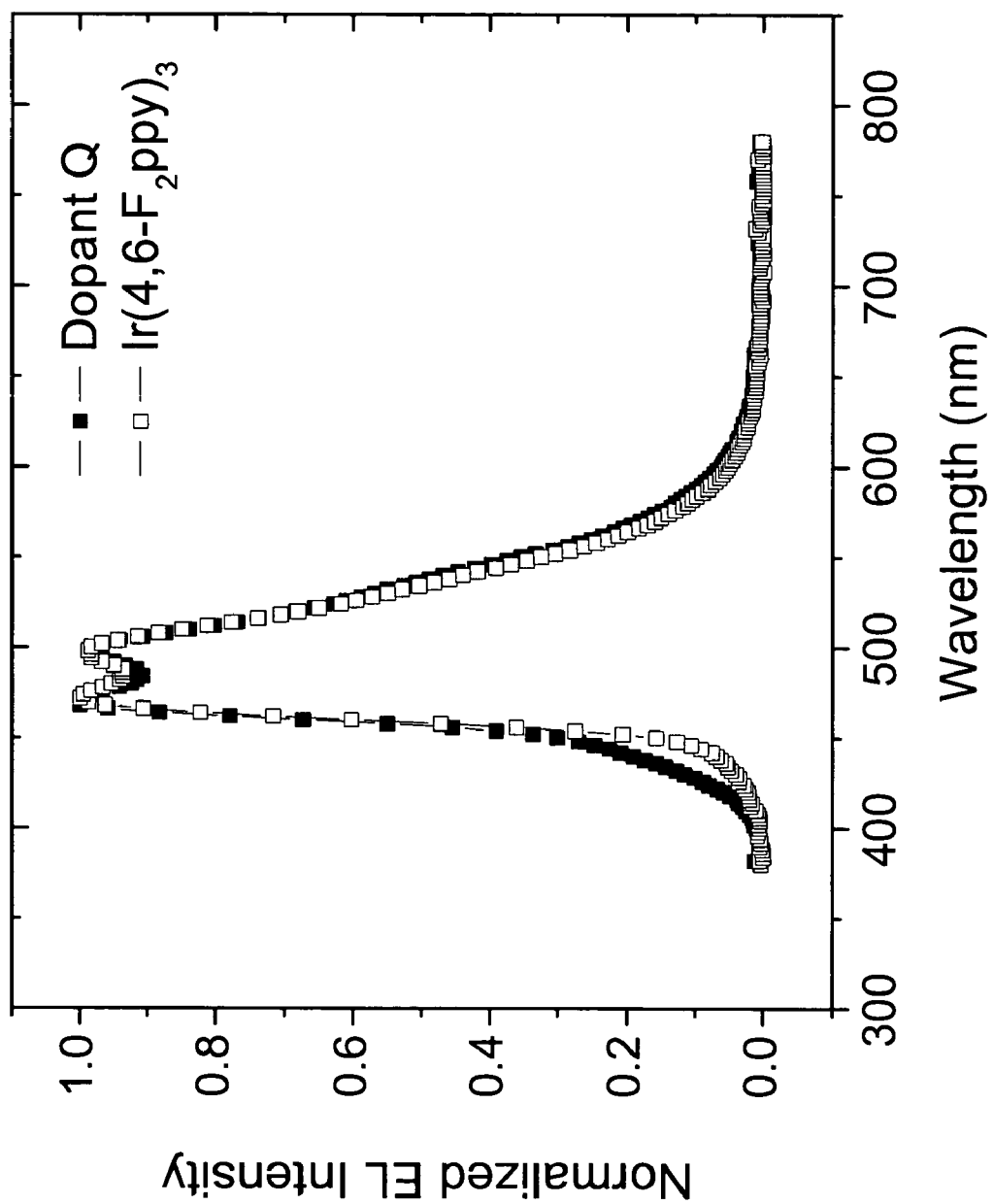
FIG. 14 shows the luminescent spectra for devices having the structures ITO/CuPc(100 Å)/NPD(300 Å)/mCP:Dopant Q (6%, 300 Å)/BAlq(400 Å)/LiF(10 Å)/Al(1000 Å) and ITO/CuPc(100 Å)/NPD(300 Å)/mCP:Ir(4,6-F$_2$ppy)$_3$ (6%, 300 Å)/BAlq(400 Å)/LiF(10 Å)/Al(1000 Å).
Figure 15:
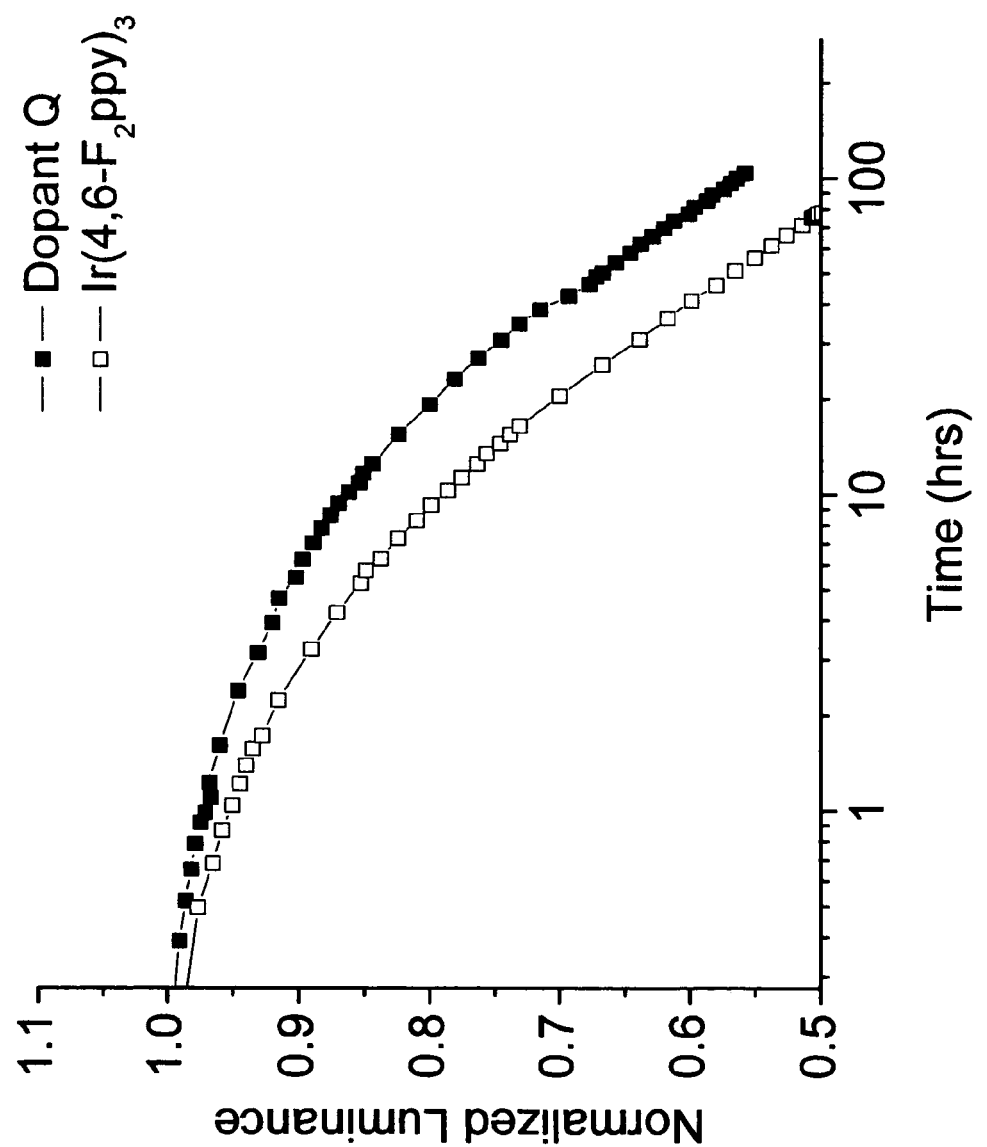
FIG. 15 shows the normalized luminance vs time for devices having the structure ITO/CuPc(100 Å)/NPD(300 Å)/mCP:Dopant Q (6%, 300 Å)/BAlq(400 Å)/LiF(10 Å)/Al (1000 Å) and ITO/CuPc(100 Å)/NPD(300 Å)/mCP:Ir(4,6-F$_2$ppy)$_3$ (6%, 300 Å)/BAlq(400 Å)/LiF(10 Å)/Al(1000 Å).

A comparison of the lifetime data can be seen in FIG. 11. The devices were driven to 50% initial luminance at a constant direct current drive of 40 mA/cm$^2$ at room temperature. The Dopant M and Dopant F devices were found to have lifetimes of ~300 hrs and ~200 hrs, respectively, compared to a lifetime ~130 hrs of the Ir(ppy)$_3$ device. As in Example 4, the results indicate that the complexes with linked ligands of the present invention exhibit enhanced stability since the Dopant F and Dopant M devices both degraded less than the device doped with a complex with unlinked ligands of Comparative Example 1.

Dopant M is a hexadentate iridium 2-phenylpyridine (ppy) complex analogous to Dopant F except that Dopant M is linked through the phenyl rings while Dopant F is linked through the pyridine rings. In general, it is believed that tethering the ligands of metal chelate complexes improves the stability with respect to ligand dissociation degradation pathways. These pathways may occur both thermally (for example, during fabrication at temperatures compatible with OLED manufacturing processes) and electrochemically (for example, oxidation/reduction during device operation). In this Example, a comparison of these two analogous hexadentate ligands indicates that linking through the phenyl rings may lower the rate of ligand dissociation even more effectively than linking through the pyridine rings. These observations may indicate a ligand dissociation pathway through Ir-C (phenyl ring) bond cleavage.

EXAMPLE 7

Synthesis of Dopant Q

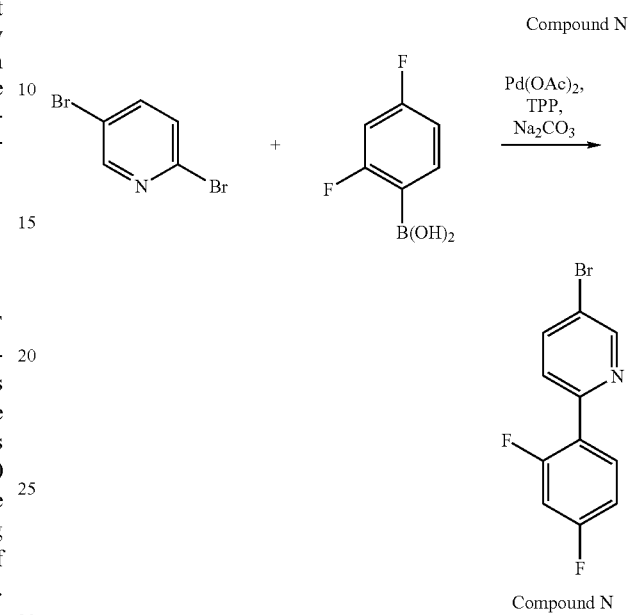

Approximately 300 mL of 1,2-dimethoxyethane and 200 mL of water were added to a 1000 mL round bottom flask. To this mixture, 30.0 g of 2,5-dibromopyridine, 20.0 g of 2,4-difluorophenylboronic acid, 0.71 g of palladium (II) acetate, and 3.3 g of triphenylphosphine, and 36.3 g of sodium carbonate were added. This mixture was heated to reflux under nitrogen atmosphere for 16 hours. After the reaction was cooled, 200 mL water and 200 mL ethyl acetate were added. The mixture was added to a separatory funnel and the organic and aqueous layers were allowed to separate. The organic layer was then washed with brine and dried over magnesium sulfate. After removal of the solvents by rotary evaporation, the crude mixture was purified by silica gel column chromatography using 10% EtOAc/Hexanes as the eluent. The fractions containing the desired product were combined and the solvent was removed by rotary evaporation. The product was crystallized from dichloromethane and hexanes. 20 g of a white solid was obtained.

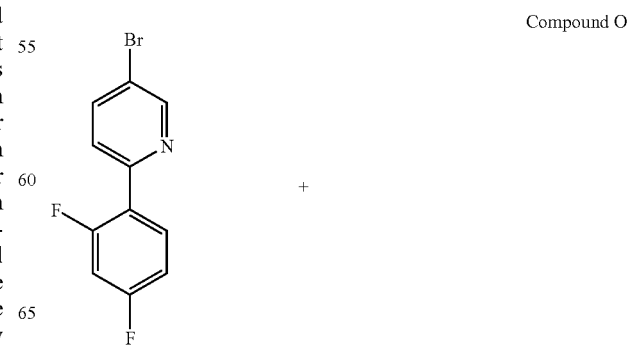

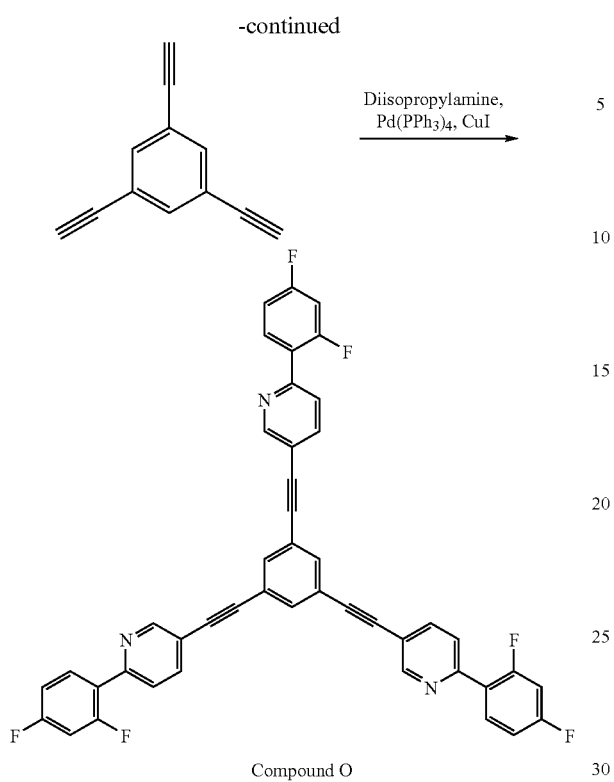

Compound O

Approximately 100 mL of dry toluene, 100 mL dry diisopropylamine, 15.0 g of Compound N, and 1.9 g of tetrakis (triphenylphosphine) palladium were added to a 500 mL round bottom flask. This mixture was heated to 60° C. for 30 minutes and then 2.8 grams of 1,3,5 triethynylbenzene and 0.21 grams of copper (I) iodide were added. The reaction was maintained at 60° C. for 12 hours and then allowed to cool. The solids were filtered and redispersed in refluxing dichloromethane. The slurry was filtered and dried to yield 12 g of a white solid.

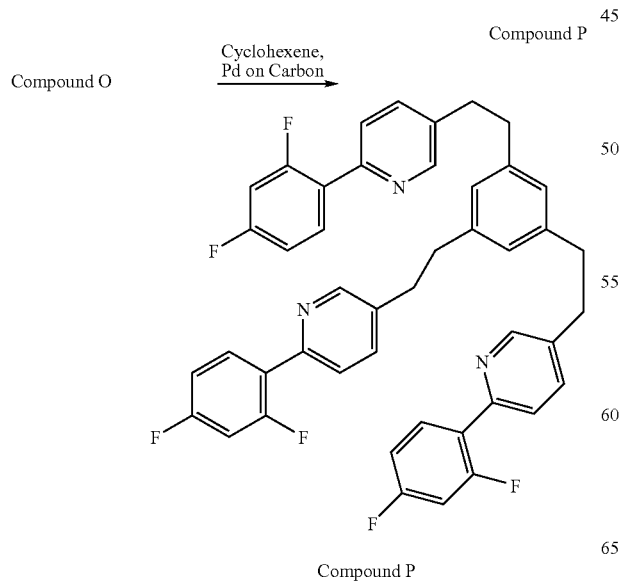

Compound P

Approximately 100 mL cyclohexene, 100 mL tetrahydrofuran, 6.0 g of 10% Pd on Carbon, and 12 g of Compound O were added to a 250 mL round bottom flask. The reaction mixture was heated to reflux for 24 hours and then allowed to cool. The solids were removed by filtration and the solvent removed from the filtrate by rotary evaporation. The product was purified by silica gel column chromatography using 60% hexanes/ethyl acetate as the eluent. The fractions containing the desired product were combined and the solvent was removed by rotary evaporation. The pure product was crystallized from ethyl acetate/hexanes and filtered to yield 8.0 g of a white solid.

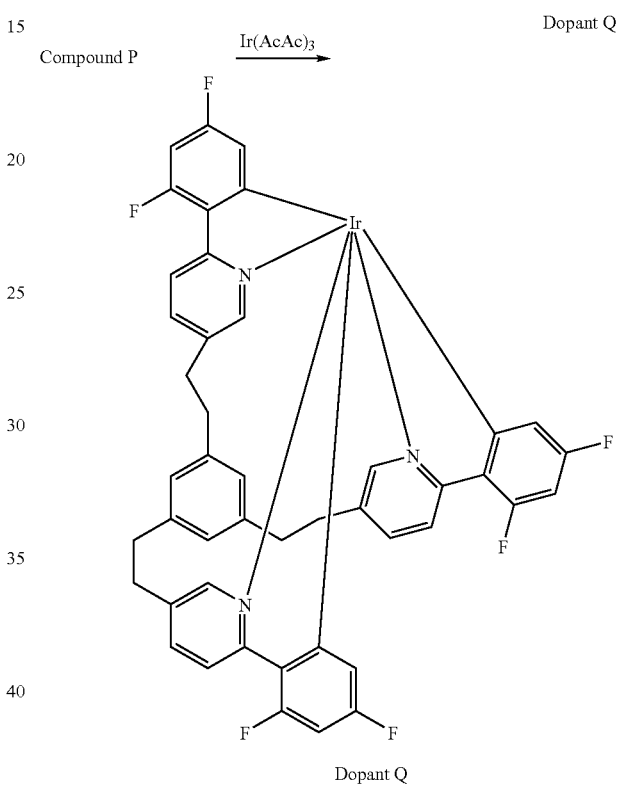

Dopant Q

Approximately 250 mL of ethylene glycol, 1.55 g of Ir(AcAc)$_3$, and 2.3 grams of compound P were added to a 500 mL round bottom flask. The reaction was heated to reflux under N$_2$ for 18 hours and then allowed to cool. Methanol was added and the yellow solids were filtered. The solids were dissolved in refluxing 1,2-dichlorobenzene and allowed to cool. The solids were filtered to yield 1.5 g of yellow product, which was confirmed by mass spectroscopy and NMR. The product was further purified by sublimation.

EXAMPLE 8

Device Comparison

Linked Ligand Device. In the Dopant Q device, the organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of N,N'-dicarbazolyl-3,5-benzene (mCP) doped with 6 wt % of Dopant Q as the emissive layer (EML). The ETL2 is 400 Å of aluminum(III)bis(2-methyl-8-quinolinato)4-phenylphenolate (BAlq). There was no ETL1.

COMPARATIVE EXAMPLE 2

In the unlinked comparative example, the organic stack consisted of 100 Å thick of copper phthalocyanine (CuPc) as the hole injection layer (HIL), 300 Å of 4,4'-bis[N-(1-naphthyl)-N-phenylamino]biphenyl (α-NPD), as the hole transporting layer (HTL), 300 Å of N,N'-dicarbazolyl-3,5-benzene (mCP) doped with 6 wt % of Ir(4,6-F$_2$ppy)$_3$ as the emissive layer (EML). The ETL2 is 400 Å of aluminum (III)bis(2-methyl-8-quinolinato)4-phenylphenolate (BAlq). There was no ETL1.

Devices were fabricated similarly to those in Example 4. The current-voltage plot, external quantum efficiency vs current density, electroluminescence spectra, and room temperature operational stability (constant current of 5 mA/cm$^2$) in terms of normalized electroluminescence vs time of the Dopant Q device and Comparative Example 2 [Ir(4,6-F$_2$ppy)$_3$] are shown in FIG. 12, FIG. 13, FIG. 14 and FIG. 15 respectively. The efficiency of the devices containing the ligand-linked complex (Dopant Q) is lower than that of the unlinked analog Comparative Example 2 [Ir(4,6-F$_2$ppy)$_3$]. However, the operational stability the devices containing the ligand-linked complex (Dopant Q) is similar to that of the unlinked analog Comparative Example 2 [Ir(4,6-F$_2$ppy)$_3$]. In this case, there is very little or no improvement in lifetime between devices containing the linked and unlinked complexes. However, as shown in Examples 4 and 6, devices containing the linked versions of the Ir(ppy)3 type complex clearly exhibit enhanced stability compared to the unlinked Ir(ppy)3. The lack of improvement in the Ir(4,6-F$_2$ppy)$_3$ type complex may be due to the electrochemical instability of fluorine substituents, which perhaps results in ligand degradation due to the reductive elimination of fluorine upon device operation. The enhanced chelating effect of the ligand to the metal center which is believed to improve the stability of the complex may not have a significant effect in such a degradation mechanism. A further possibility is that the degradation mechanism occurs primarily through the cleavage of the Ir—C bond. As shown in Example 6, Dopant M, where the ligands are linked through the phenyl ring, are more stable than devices using dopant F, with ligands linked through the pyridine ring. If this is the case, linking the ligands through the pyridine rings may not show a significant improvement in stability for high energy dopants substituted with fluorine, such as Dopant Q.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. An organic light emitting device comprising an anode, a cathode, and an organic layer disposed between the anode and the cathode, wherein the organic layer comprises a phosphorescent organometallic emissive material comprising
   a transition metal, Tl, Pb, Bi, In, Sn, Sb or Te, and
   two or three bidentate ligands, wherein two or more of the bidentate ligands are covalently linked by a linking group,
   wherein, the bidentate ligands are selected from bidentate photoactive ligands, wherein each bidentate photoactive ligand is bound to the transition metal, Tl, Pb, Bi, In, Sn, Sb or Te through a carbon-metal bond and a nitrogen-metal bond to form a cyclometallated ring, and bidentate ancillary ligands,
   wherein at least one of the bidentate ligands is a bidentate photoactive ligand.

2. The organic light emitting device of claim 1, wherein the linking group provides no π-conjugation between the linked bidentate ligands.

3. The organic light emitting device of claim 1 wherein the transition metal is selected from the group consisting of Ir, Pt, Pd, Rh, Re, Os, Au, and Ag.

4. The organic light emitting device of claim 1 wherein the transition metal is Ir.

5. An organic light emitting device comprising an anode, a cathode, and an organic layer disposed between the anode and the cathode, wherein the organic layer comprises an emissive material of the formula I $$[X_a\text{—}(L)_b]M \qquad (I)$$

wherein
M is a transition metal having a molecular weight greater than 40, Tl, Pb, Bi, In, Sn, Sb or Te;
X is a linking group that links two or more L, and is selected from the group consisting of —(CR$_2$)$_d$—, —[O(CR$_2$)$_e$]O—, or a group having the formula

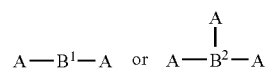

wherein
A is —(CR$_2$)$_f$, or -Z-(CR$_2$)$_g$—;
Z is —O—, —NR—, or —SiR$_2$—;
B$^1$ is —O—, —NR—, —CR=CR—, aryl, heteroaryl,
B$^2$ is

alkyl, aryl, heteroaryl, cycloalkyl, or a heterocyclic group;
each R is independently selected from H, alkyl, aralkyl, aryl and heteroaryl,
d is 1 to 6,
e is 1 to 6,
f is 1 to 4, and
g is 1 to 4;
L is a bidentate ligand selected from the group consisting of
(i) bidentate photoactive ligands having the formula II

wherein
the bidentate photoactive ligand is bound to the transition metal, Tl, Pb, Bi, In, Sn, Sb or Te through a carbon-metal bond and a nitrogen-metal bond to form a cyclometallated ring, Y is N or C, the dotted line represents an optional double bond, $R^1$, $R^2$, $R^3$ and $R^4$ are independently selected from H, alkyl, or aryl, and additionally or alternatively, one or more of $R^1$ and $R^2$, $R^2$ and $R^3$, and $R^3$ and $R^4$ together from independently a 5 or 6-member cyclic group, wherein said cyclic group is cycloalkyl, cycloheteroalkyl, aryl or heteroaryl; and wherein said cyclic group is optionally substituted by one or more substituents Z;

each substituent Z is independently selected from the group consisting of alkyl, alkenyl, alkynyl, aralkyl, CN, $CF_3$, $NR_2$, $NO_2$, OR, halo, and aryl, and additionally, or alternatively, two Z groups on adjacent ring atoms form a fused 5- or 6-membered aromatic group, and each R is independently selected from H, alkyl, aralkyl, aryl and heteroaryl; and (ii) bidentate ancillary ligands, a is 1 to 4;

b is 2 or 3; and at least one L is selected from a bidentate photoactive ligand.

6. The organic light emitting device of claim 5, wherein the photoactive ligands are selected from compounds of the formula IV

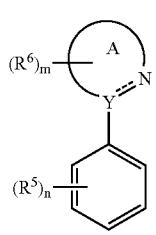

(IV)

wherein:

ring A is an aromatic heterocyclic ring or a fused aromatic heterocyclic ring with at least one nitrogen atom that coordinates to the metal M, Y is selected from carbon or nitrogen, each $R^5$ is independently selected from the group consisting of alkyl, alkenyl, alkynyl, aralkyl, CN, $CF_3$, $NR_2$, $NO_2$, OR, halo, and aryl, and additionally, or alternatively, two $R^5$ groups on adjacent ring atoms form a fused 5- or 6-membered aromatic group, each $R^6$ is independently selected from the group consisting of alkyl, alkenyl, alkynyl, aralkyl, CN, $CF_3$, $NR_2$, $NO_2$, OR, halo, and aryl, and additionally, or alternatively, two $R^6$ groups on adjacent ring atoms form a fused 5- or 6-membered aromatic group, each R is independently selected from H, alkyl, aralkyl, aryl and heteroaryl, n is 0 to 4, and m is 0 to 4.

7. The organic light emitting device of claim 5, wherein $[X_a-(L)_b]$ has the formula:

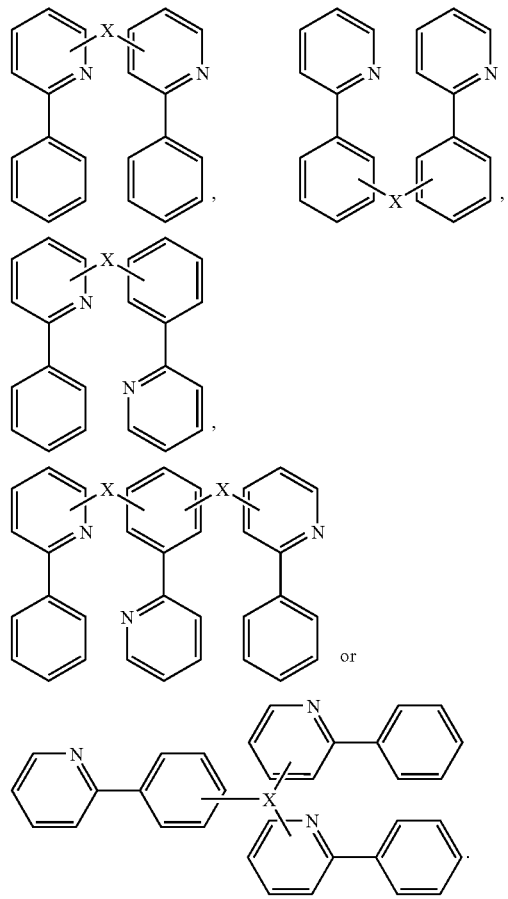

8. The organic light emitting device of claim 5, wherein the emissive material is a compound having the formula

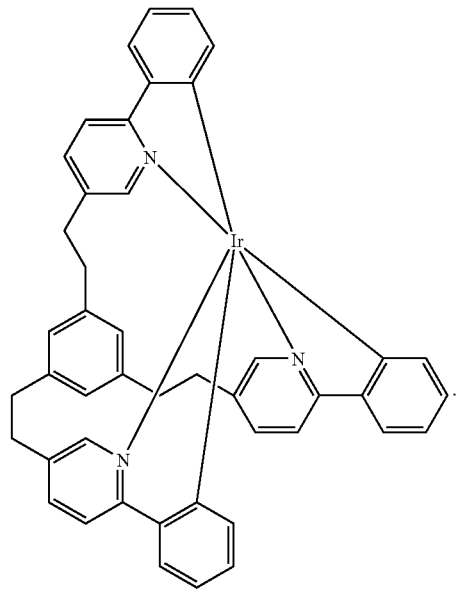

9. The organic light emitting device of claim 5, wherein the emissive material is a compound having the formula

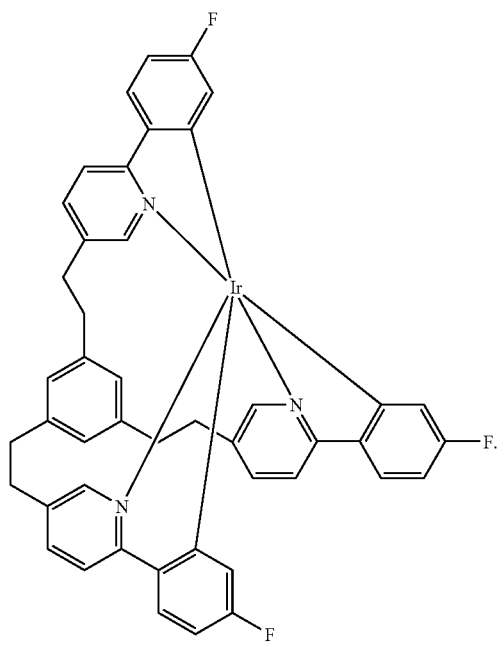

10. The organic light emitting device of claim 5, wherein the emissive material is a compound having the formula

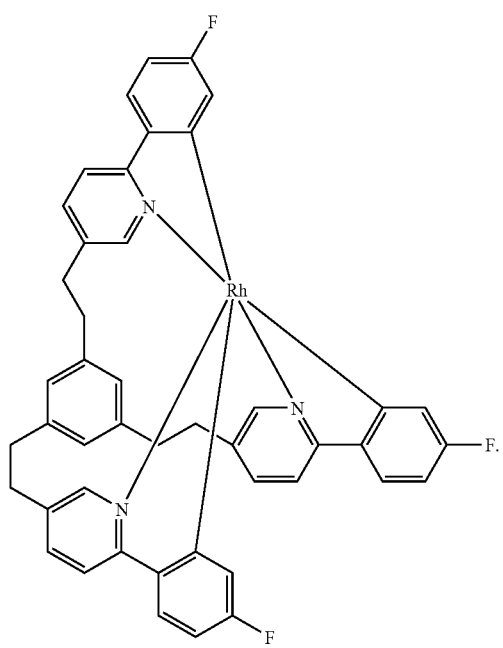

11. The organic light emitting device of claim 5, wherein $[X_a\text{—}(L)_b]$ has the formula:

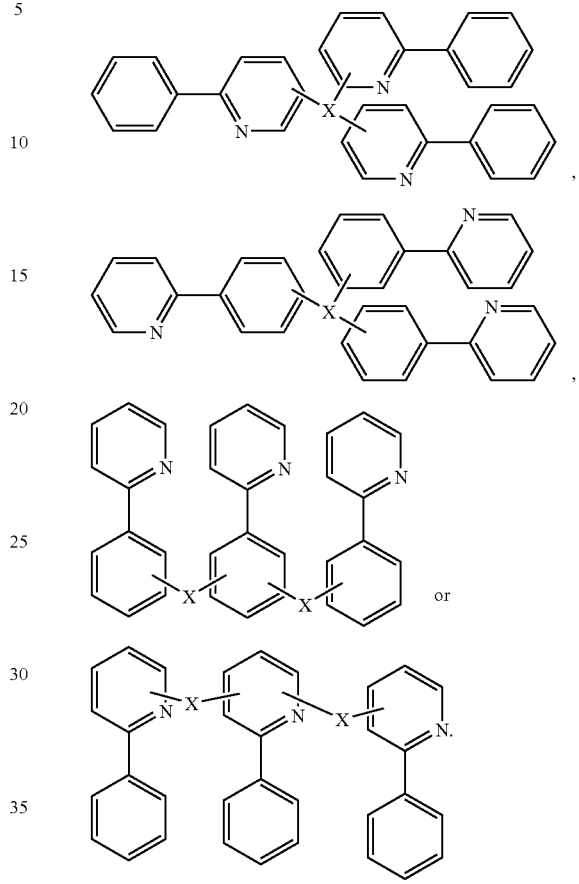

12. The organic light emitting device of claim 5, wherein $[X_a\text{—}(L)_b]$ has the formula:

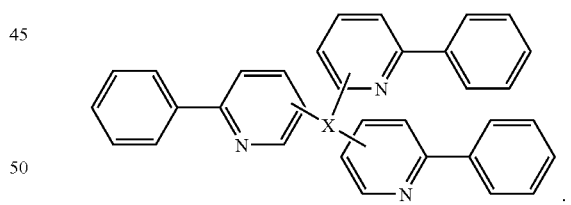

13. The organic light emitting device of claim 5, wherein $[X_a\text{—}(L)_b]$ has the formula:

14. The organic light emitting device of claim 5, wherein the emissive material is a compound having the formula

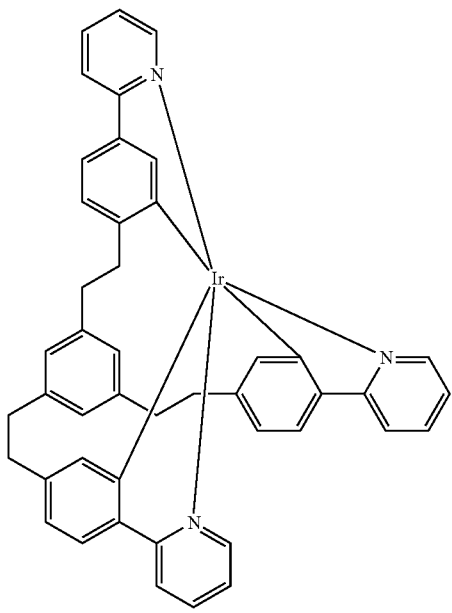

15. The organic light emitting device of claim 5, wherein the emissive material is a compound having the formula:

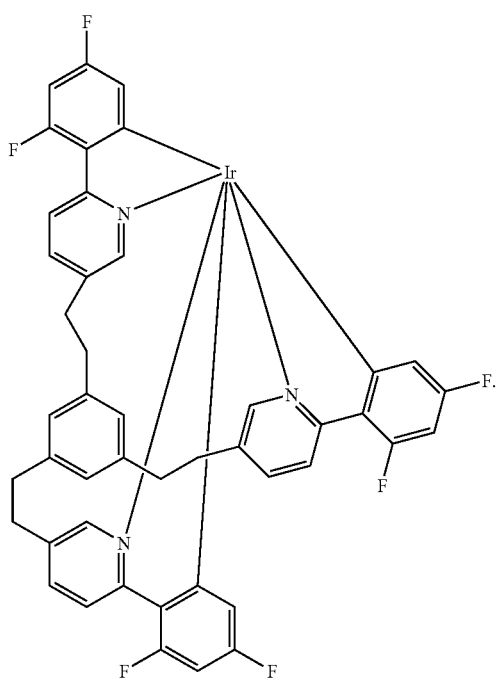

16. The organic light emitting device of claim 5, wherein two or more L comprise a phenyl moiety and X is a linking group that links the two or more L via a covalent bond to the phenyl moiety in each of the two or more L.

17. The organic light emitting device of claim 5, wherein [$X_a$—(L)$_b$] has the formula

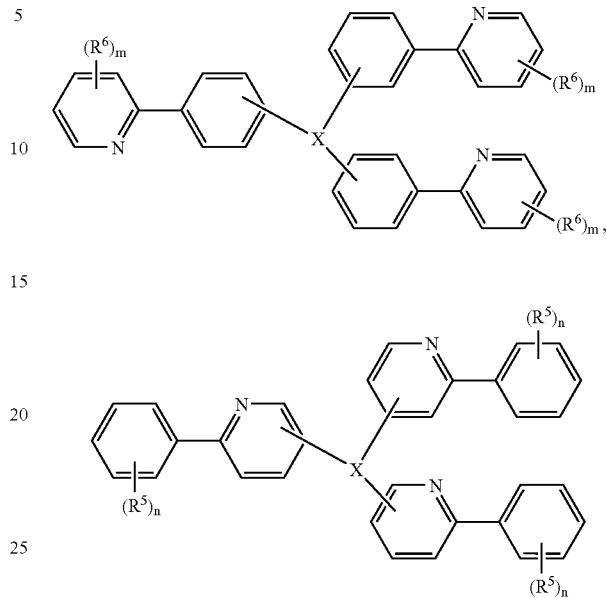

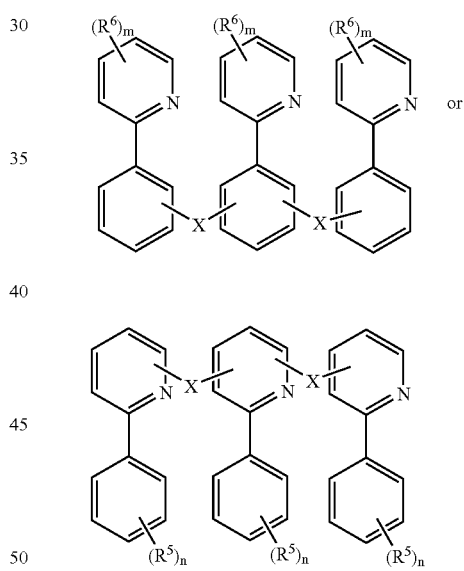

wherein each $R^5$ is independently selected from the group consisting of alkyl, alkenyl, alkynyl, aralkyl, CN, $CF_3$, $NR_2$, $NO_2$, OR, halo, and aryl, and additionally, or alternatively, two $R^5$ groups on adjacent ring atoms form a fused 5- or 6-membered aromatic group, each $R^6$ is independently selected from the group consisting of alkyl, alkenyl, alkynyl, aralkyl, CN, $CF_3$, $NR_2$ $NO_2$ OR, halo, and aryl, and additionally, or alternatively, two $R^6$ groups on adjacent ring atoms form a fused 5- or 6-membered aromatic group, each R is independently selected from H, alkyl, aralkyl, aryl and heteroaryl, n is 0 to 4, and m is 0 to 4.

18. The organic light emitting device of claim 17, wherein [X$_a$—(L)$_b$] has the formula:

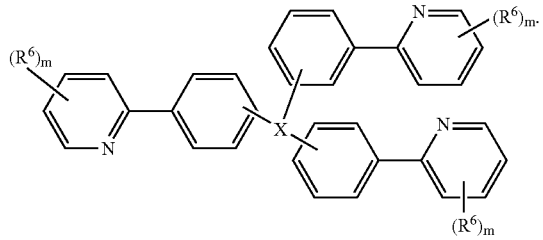

19. The organic light emitting device of claim 17, wherein [X$_a$—(L)$_b$] has the formula:

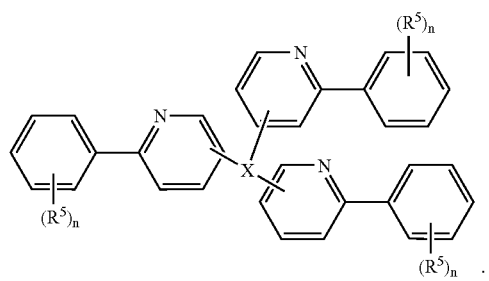

20. The organic light emitting device of claim 5 wherein the transition metal is selected from the group consisting of Ir, Pt, Pd, Rh, Re, Os, Au, and Ag.

21. The organic light emitting device of claim 5 wherein the transition metal is Ir.

22. A compound of the formula I

[X$_a$—(L)$_b$]M  (I)

wherein,
M is a transition metal having a molecular weight greater than 40, Tl, Pb, Bi, In, Sn, Sb or Te;
X is a linking group that links two or more L, and is selected from the group consisting of —(CR$_2$)$_d$—, —[O(CR$_2$)$_e$]O—, or a group having the formula

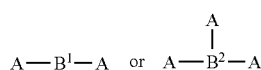

wherein
A is —(CR$_2$)$_f$, or -Z-(CR$_2$)$_g$—;
Z is —O—, —NR—, or —SiR$_2$—;
B$^1$ is —O—, —NR—, —CR=CR—, aryl, heteroaryl, cycloalkyl, or a heterocyclic group,
B$^2$ is

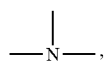 , 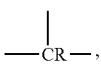 , alkyl, aryl, heteroaryl, cycloalkyl, or a heterocyclic group;
each R is independently selected from H, alkyl, aralkyl, aryl and heteroaryl,
d is 1 to 6,
e is 1 to 6,
f is 1 to 4, and
g is 1 to 4;
L is a bidentate ligand selected from the group consisting of
(i) bidentate photoactive ligands having the formula II

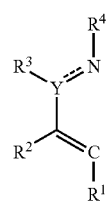

wherein
the bidentate photoactive ligand is bound to the transition metal, Tl, Pb, Bi, In, Sn, Sb or Te through a carbon-metal bond and a nitrogen-metal bond to form a cyclometallated ring,
Y is N or C,
the dotted line represents an optional double bond,
R$^1$, R$^2$, R$^3$ and R$^4$ are independently selected from H, alkyl, or aryl, and additionally or alternatively, one or more of R$^1$ and R$^2$, R$^2$ and R$^3$, and R$^3$ and R$^4$ together from independently a 5 or 6-member cyclic group, wherein said cyclic group is cycloalkyl, cycloheteroalkyl, aryl or heteroaryl; and wherein said cyclic group is optionally substituted by one or more substituents Z;
each substituent Z is independently selected from the group consisting of alkyl, alkenyl, alkynyl, aralkyl, CN, CF$_3$, NR$_2$, NO$_2$, OR, halo, and aryl, and additionally, or alternatively, two Z groups on adjacent ring atoms form a fused 5- or 6-membered aromatic group, and
(ii) bidentate ancillary ligands,
each R is independently selected from H, alkyl, aralkyl, aryl and heteroaryl;
a is 1 to 4;
b is 2 or 3; and
at least one L is selected from a bidentate photoactive ligand.

23. The compound of claim 22, wherein the photoactive ligands are selected from compounds of the formula IV

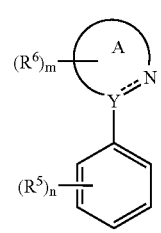

wherein:
- ring A is an aromatic heterocyclic ring or a fused aromatic heterocyclic ring with at least one nitrogen atom that coordinates to the metal M,
- Y is selected from carbon or nitrogen,
- each $R^5$ is independently selected from the group consisting of alkyl, alkenyl, alkynyl, aralkyl, CN, $CF_3$, $NR_2$, $NO_2$, OR, halo, and aryl, and additionally, or alternatively, two $R^5$ groups on adjacent ring atoms form a fused 5- or 6-membered aromatic group,
- each $R^6$ is independently selected from the group consisting of alkyl, alkenyl, alkynyl, aralkyl, CN, $CF_3$, $NR_2$, $NO_2$, OR, halo, and aryl, and additionally, or alternatively, two $R^6$ groups on adjacent ring atoms form a fused 5- or 6-membered aromatic group, each R is independently selected from H, alkyl, aralkyl, aryl and heteroaryl,
- n is 0 to 4, and
- m is 0 to 4.

24. The compound of claim 22, wherein $[X_a—(L)_b]$ has the formula:

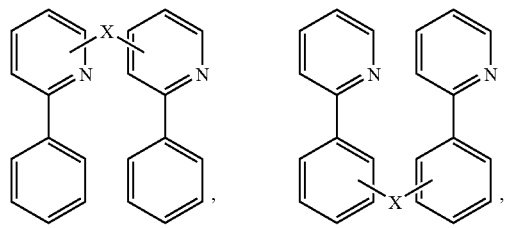

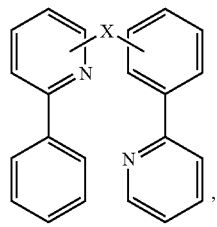

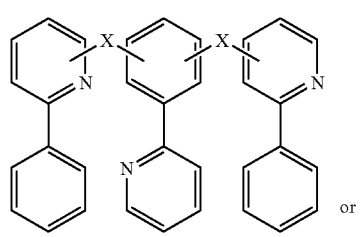

or

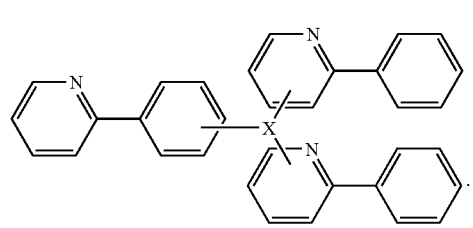

25. The compound of claim 22, having the formula

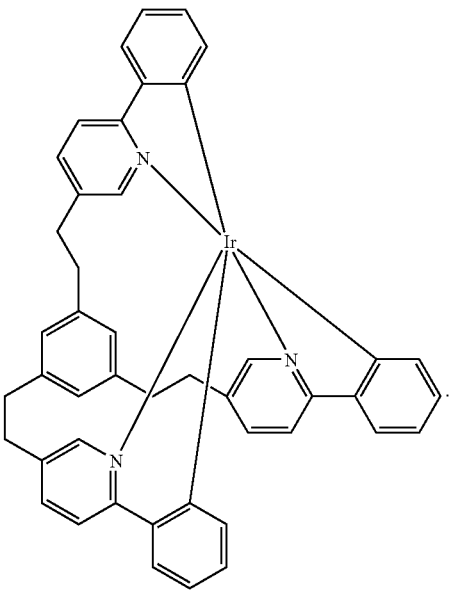

26. The compound of claim 22, having the formula

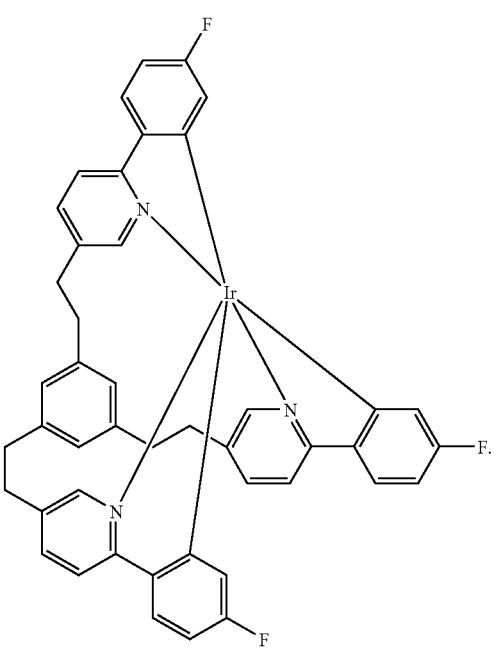

27. The compound of claim 22, having the formula
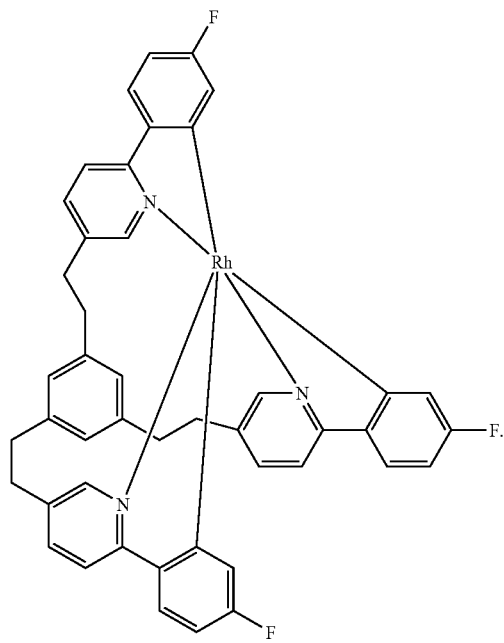
28. The compound of claim 22, wherein [$X_a$—(L)$_b$] has the formula:
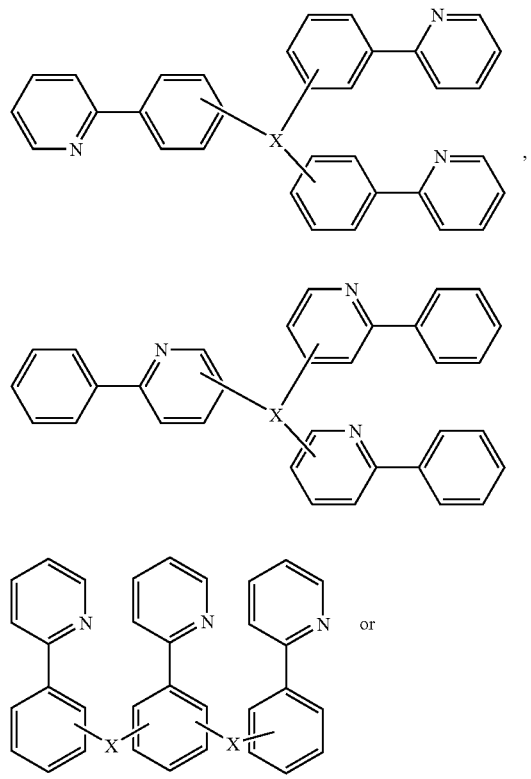
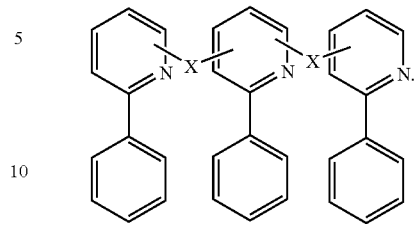
29. The compound of claim 22, wherein [$X_a$—(L)$_b$] has the formula:
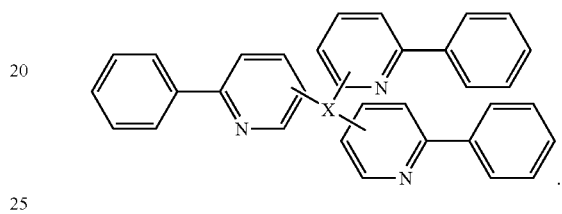
30. The compound claim 22, wherein [$X_a$—(L)$_b$] has the formula:
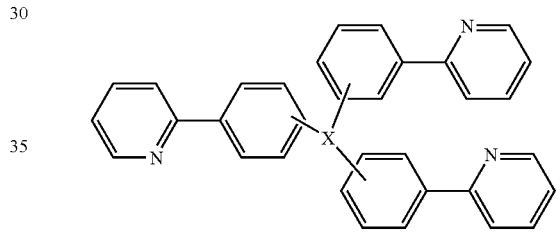
31. The compound of claim 22, having the formula:
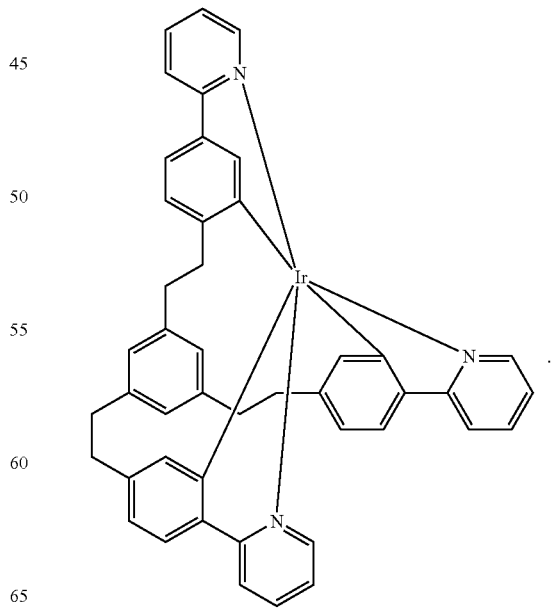

32. The compound of claim 22 having the formula:

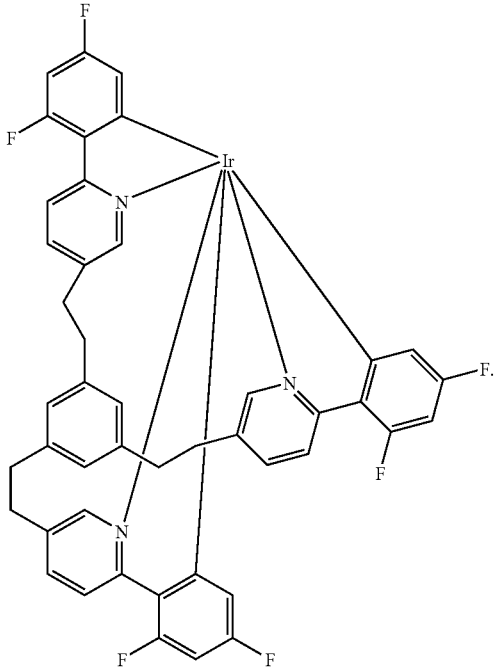

33. The compound of claim 22, wherein X is linked to each L via a covalent bond to a pyridyl moiety in each L.

34. The compound of claim 22, wherein [$X_a$—(L)$_b$] has the formula:

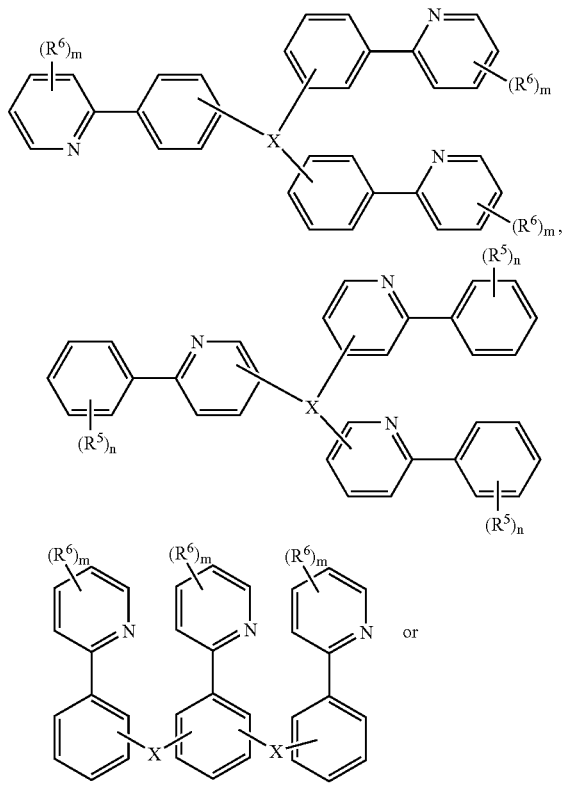

-continued

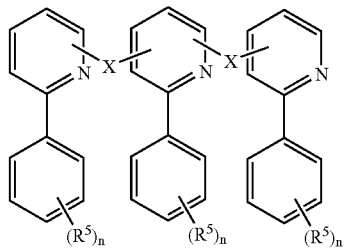

each $R^5$ is independently selected from the group consisting of alkyl, alkenyl, alkynyl, aralkyl, CN, $CF_3$, $NR_2$, $NO_2$, OR, halo, and aryl, and additionally, or alternatively, two $R^5$ groups on adjacent ring atoms form a fused 5- or 6-membered aromatic group, each $R^6$ is independently selected from the group consisting of alkyl, alkenyl, alkynyl, aralkyl, CN, $CF_3$, $NR_2$, $NO_2$, OR, halo, and aryl, and additionally, or alternatively, two $R^6$ groups on adjacent ring atoms form a fused 5- or 6-membered aromatic group, each R is independently selected from H, alkyl, aralkyl, aryl and heteroaryl,
n is 0 to 4, and
m is 0 to 4.

35. The compound of claim 34, wherein [$X_a$—(L)$_b$] has the formula:

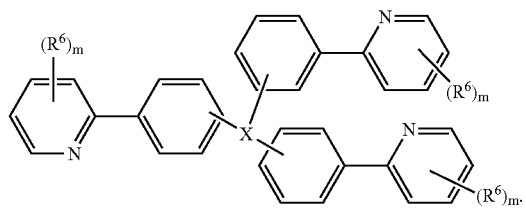

36. The compound of claim 34, wherein [$X_a$—(L)$_b$] has the formula:

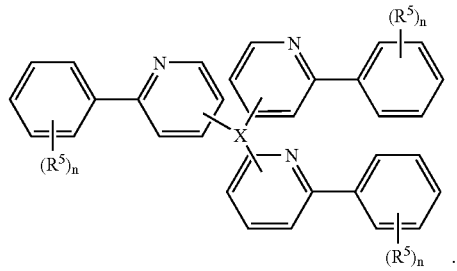

37. The compound of claim 22 wherein the transition metal is selected from the group consisting of Ir, Pt, Pd, Rh, Re, Os, Au, and Ag.

38. The compound of claim 22 wherein the transition metal is Ir.

39. An organic light emitting device comprising an anode, a cathode, and an organic layer disposed between the anode and the cathode, wherein the organic layer comprises a metal complex comprising:
  a metal;
  a first ligand bound to the metal, wherein the first ligand is a bidentate ligand;
  a second ligand bound to the metal; and a linking group that covalently links the first ligand and the second ligand,
wherein the linking group provides no iL-conjugation between the first ligand and the second ligand;
and wherein the metal complex is a phosphorescent organometallic emissive material.

40. The organic light emitting device of claim 39, wherein the second ligand is a monodentate ligand.

41. An organic light emitting device comprising an anode, a cathode, and an organic layer disposed between the anode and the cathode, wherein the organic layer comprises a phosphorescent organometallic emissive material comprising a metal bound to two or three bidentate ligands, wherein two or more of the bidentate ligands are covalently linked by one or more linking groups.

42. The organic light emitting device of claim 41 wherein the organometallic emissive material comprises a compound represented by the formula $[X_a\text{—}(L)_b]M$ wherein M is a transition metal, Tl, Pb, Bi, In, Sn, Sb, or Te; L is a bidentate ligand;
X is a linking group that links two or more L;
a is 1 to 4;
b is 2 or 3;
wherein the bidentate ligands are selected from bidentate photoactive ligands, and bidentate ancillary ligands wherein at least one of the bidentate ligands is a bidentate photoactive ligand.

43. The organic light emitting device of claim 42 wherein the transition metal is selected from the group consisting of Ir, Pt, Pd, Rh, Re, Os, Au, and Ag.

44. The organic light emitting device of claim 42 wherein the transition metal is Ir.

45. A compound of the formula $[X_a\text{—}(L)_b]M$ wherein M is a transition metal, Tl, Pb, Bi, In, Sn, Sb or Te; L is a bidentate ligand; X is a linking group that links two or more L;
a is 1 to 4,
b is 2 or 3
wherein the bidentate ligands are selected from bidentate photoactive ligands, and bidentate ancillary ligands wherein at least one of the bidentate ligands is a bidentate photoactive ligand bound to the transition metal, Tl, Pb, Bi, In, Sn. Sb or Te through a carbon-metal bond; and
wherein the compound is a phosphorescent emissive material.

46. The compound of claim 45 wherein the transition metal is selected from the group consisting of Ir, Pt, Pd, Rh, Re, Os, Au, and Ag.

47. The compound of claim 45 wherein the transition metal is Ir.

* * * * *